United States Patent [19]
Deaton et al.

[11] Patent Number: 6,128,918
[45] Date of Patent: Oct. 10, 2000

[54] CONTAINERS FOR HYPERPOLARIZED GASES AND ASSOCIATED METHODS

[75] Inventors: Daniel M. Deaton, Raleigh; Patrick A. Cella, Raleigh; Kenton C. Hasson, Durham; David Zollinger, Chapel Hill; Bastiaan Driehuys, Durham, all of N.C.

[73] Assignee: Medi-Physics, Inc., Princeton, N.J.

[21] Appl. No.: 09/126,448

[22] Filed: Jul. 30, 1998

[51] Int. Cl.$^7$ ................................................ F25J 1/00
[52] U.S. Cl. ................................ 62/610; 62/45.1; 62/919
[58] Field of Search .............................. 62/45.1, 610, 919

[56] References Cited

U.S. PATENT DOCUMENTS

| | | | |
|---|---|---|---|
| 2,413,243 | 12/1946 | Neff | 62/45.1 |
| 2,889,953 | 6/1959 | Morrison | 62/45.1 |
| 2,916,058 | 12/1959 | Unthank | 62/45.1 |
| 3,050,208 | 8/1962 | Irvine | 62/45.1 |
| 3,657,363 | 4/1972 | Dorko | 260/642 |
| 3,748,864 | 7/1973 | Lofredo et al. | 62/22 |
| 3,966,781 | 6/1976 | Atkinson et al. | 260/410.9 R |
| 4,080,429 | 3/1978 | Koeppe et al. | 423/262 |
| 4,369,048 | 1/1983 | Pence | 55/66 |
| 4,417,909 | 11/1983 | Weltmer, Jr. | 62/12 |
| 4,586,511 | 5/1986 | Clark, Jr. | 128/653 |
| 4,599,462 | 7/1986 | Michl | 568/702 |
| 4,755,201 | 7/1988 | Eschwey et al. | 62/12 |
| 4,914,160 | 4/1990 | Azizian | 525/329.3 |
| 4,977,749 | 12/1990 | Sercel | 62/51.1 |
| 5,007,243 | 4/1991 | Yamaguchi et al. | 62/51.1 |
| 5,039,500 | 8/1991 | Shino et al. | 423/262 |
| 5,161,382 | 11/1992 | Missimer | 62/46.1 |
| 5,545,396 | 8/1996 | Albert et al. | 424/93 |
| 5,612,103 | 3/1997 | Driehuys et al. | 428/34.7 |
| 5,617,860 | 4/1997 | Chupp et al. | 128/653.4 |
| 5,642,625 | 7/1997 | Cates, Jr. et al. | 62/55.5 |

FOREIGN PATENT DOCUMENTS

| | | |
|---|---|---|
| 2091884 | 8/1982 | United Kingdom . |
| PCT/US97/ 05004 | 3/1997 | WIPO . |
| PCT/US97/ 05084 | 3/1997 | WIPO . |

(List continued on next page.)

OTHER PUBLICATIONS

Gregory et al., "Pore–structure determinations of silica aerogels by $^{129}$Xe NMR spectroscopy and imaging," J. of Mag. Res., vol. 131, pp. 327–335 (1998).

Mansfeld et al., "The use of $^{129}$Xe NMR exchange spectroscopy for probing the microstructure of porous materials," Chem, Phys, Ltrs., vol. 213, No. 1,2, pp. 153–157.(Oct. 1, 1993.

Pasquier et al., "$^{129}$Xe NMR as a probe of the dynamics of gas confined in porus Vycor," Mag. Res. Imaging, vol. 14, No. 7/8 pp.971–973 (1996).

(List continued on next page.)

*Primary Examiner*—Ronald Capossela
*Attorney, Agent, or Firm*—Myers Bigel Sibley & Sajovec, P.A.

[57] ABSTRACT

A resilient container configured to receive a quantity of hyperpolarized noble gas includes a wall with at least two layers, a first layer with a surface which minimizes spin-relaxation and a first or second layer which is substantially impermeable to oxygen. The container is especially suitable for collecting and transporting $^3$He. The resilient container can be configured to directly deliver the hyperpolarized noble gas to a target interface by deflating or collapsing the inflated resilient container. Related collection and transporting methods include forming the wall of the container and collecting the hyperpolarized gas in a way which minimizes its exposure to de-polarizing impurities. Also, a container includes a quantity of polarized gas and extends the $T_1$ life by configuring the wall of the container with a controlled thickness of the surface coating and overlays the interior with an exterior which is substantially impermeable to oxygen. In addition, an O-ring and seal is configured to minimize the depolarizing effect of the collection device. Also disclosed is a method for determining the gas solubility in an unknown polymer or liquid using the measured relaxation time of a hyperpolarized gas.

46 Claims, 12 Drawing Sheets

FOREIGN PATENT DOCUMENTS

| | | |
|---|---|---|
| PCT/US97/05166 | 3/1997 | WIPO . |
| WO97/10018 | 3/1997 | WIPO . |
| WO97/37239 | 10/1997 | WIPO . |
| WO 99/07415 | 2/1999 | WIPO . |
| WO 99/08941 | 2/1999 | WIPO . |
| WO 99/14582 | 2/1999 | WIPO . |
| WO 99/25243 | 5/1999 | WIPO . |
| WO 99/17304 | 8/1999 | WIPO . |

OTHER PUBLICATIONS

PCT International Search Report, PCT International Application No. PCT/US99/13597, mailed Sep. 3, 2000.

De Schepper, "The HERMES $^3$He target," AIP Conf. Proc., vol. 421, No. 1, pp. 16–25 (Jan. 1998).

Pfeffer et al., "$^{129}$Xe Gas NMR Spectroscopy and Imaging with a Whole–Body Image" J. Mag. Res., Series A, 108, pp. 106–109 (1994).

Gao, J.H. et al., *Magnetization and Diffusion Effects in NMR Imaging of Hyperpolarized Substances*, Magn. Reson. Med., vol. 37, No. 1, pp. 153–158 (Jan. 1997).

Kaatz, P. et al., *A comparison of molecular Hyperpolarizabilities from gas and liquid phase measurements*; J. Chem. Phys. vol. 108, No. 3, pp. 849–856 (Jan. 15, 1998).

Kauczor, .U. et al., *The helium–3 MRT of pulmonary ventilation; the initial clinical applications*, Abstract, Rofo Forstchr Geb Rontgenstru Neuen Bildegeb Verfahr, vol. 166, No. 3 (Mar. 1997).

Kauczor, H. et al., *MRI using hyperpolarizd noble gases*, Abstract, Eur. Radiol., vol. 8, No. 5 (1998).

Nacher, P. J. et al., *Recent results on hyperpolarized $^3$He–$^4$He liquid mixtures*, vol. 46, Supp. Pt. S6, pp. 3025–3032 (1966).

Patyal et al., *Longitudinal Relaxation and Diffusion Measurements Using Magnetic Resonance Signals from Laser–Hyperpolarized $^{129}$Xe Nuclei*, J. Magn. Reson., vol. 126, pp. 58–65 (May 1977).

Song, Y. Q. et al., *Effects of diffusion on magnetic resonance imaging of laser–polarized xenon gas*, J. Chem. Phys., vol. 108, No. 15, pp. 6233–6239 (Apr. 15, 1998).

Albert et al., "$^{129}$Xe Relaxation Catalysis by Oxygen", *Abstracts of the 11th Annual Meeting of the Society for Magnetic Resonance Medicine*, (1992).

Albert et al., "Relaxation of $^{129}$Xe in Model Biological Systems: On Probing the Mechanism of General Anesthesia", *Abstracts of the 11th Annual Meetings of the Society for Magnetic Resonance Medicine*, (1992).

Becker et al., "Study Of Mechanical Compression Of Spin–Polarized $^3$He Gas", *Nuclear Instruments And Methods In Physics Research*, vol. A 346, pp. 45–51 (1994).

Bhaskar et al., "Efficiency of Spin Exchange between Rubidium Spins and $^{129}Xe$ $^{Nuclei\ in\ a\ Gas}$", *Physical Review Letters*, vol. 49, pp. 25–28 (1982).

Cain et al., "Nuclear Spin Relation Mechanisms and Mobility of Gases in Polymers", 94 *J. Phys. Chem.* No. 5, pp. 2128–2135 (1990).

Cates et al., "Laser Production of Large Nuclear–Spin Polarization in Frozen Xenon", *Phys. Rev. Lett.*, vol. 65, No. 20, pp. 2591–2594 (1990).

Cates et al., "Rb–$^{129}$Xe spin–exchange rates due to binary and three–body collisions at High Xe pressures", *Physical Review A*, vol. 45, pp. 4631–4639 (1992).

Cummings et al., "Optical pumpings of Rb vapor using high–power $GA_{1-x}A_xAs$ diode laser arrays", *Phys. Rev. A*, vol. 51, No. 6, pp. 4842–4851 (1995).

Driehuys et al., "High–volume production of laser–polarized $^{129}$Xe", 69 *App. Phys. Lett.* (12), pp. 1668–1670 (1996).

Driehuys et al., "Surface Relaxation Mechanisms of Laser–Polarized $^{129}$Xe", 74 *Phys. Rev. Lett.*, No. 24, pp. 4943–4946 (1995).

Freed, "Dynamic effects of pair correlation functions on spin relaxation by translational diffusion in liquids. II. Finite jumps and independent $T_1$processes", 68 *J. Chem. Phys.* vol. 9, pp. 4034–4037 (1978).

Gatzke et al., "Extraordinarily Slow Nuclear Spin Relaxation in Frozen Lazer–Polarized $^{129}$Xe", *Phys. Rev. Lett.*, vol. 70, No. 5, pp. 690–693 (1993).

Happer et al., "An Optical Pumping Primer", *Hyperfine Interactions* 38, pp. 435–470 (1987).

Heil et al., "Very long nuclear relaxation times of spin polarized helium 3 in metal coated cells", *Physics Letters A* 201, pp. 337–343 (1995).

Hunt et al., "Nuclear Magnetic Resonance of $^{129}$Xe in Natural Xenon", 130 *Phys Rev.* . pp. 2302–2305 (1963).

Hwang et al., "Dynamic effects of pair correlation functions on spin relaxation by translational diffusion in liquids", 63 *J. Chem. Phys.* No. 9, pp. 4017–4025 (1975).

Laloë, F. et al., "Workshop on Polarized $^3$He Beams and Targets", *AIP Conference Proceedings #131* (1984).

Middleton et al., "MR Imaging With Hyperpolarized $^3$He Gas", *Magnetic Resonance In Medicine*, vol. 33, pp. 271–275 (1995).

Middleton, "The Spin Structure of The Neutron Determined Using A Polarized $^3$He Target", *Ph.D. Dissertation*, Princeton University (1994).

Miller et al., "Xenon NMR: Chemical shifts of a general anesthetic common solvents, proteins, and membranes", *Proc. of the Nat. Academy of Science (USA)*, vol. 78, No. 8, pp. 4946–4949 (1981).

Mugler et al., "MR Imaging and Spectroscopy Using Hyperpolarized $^{129}$Xe Gas: Preliminary Human Results", *Magnetic Resonance in Medicine*, vol. 37, pp. 809–815 (1997).

Newbury et al., "Gaseous $^3$He–$^3$He magnetic dipolar spin relaxation", 48 *Phys. Rev. A.*, No. 6, pp. 4411–4420 (1993).

Pauly, *Permeability and Diffusion Data, The Polymer Handbook* VI/435–449.

Raftery et al., "NMR of optically pumped xenon thin films", *Chem. Phys. Lett.*, vol. 191, pp. 385–390 (1992).

Reif, "Fundamentals of Statistical and Thermal Physics", *McGraw–Hill*, Ch. 12–14, pp. 461–493 (1965).

Saam et al., "Nuclear relaxation of $^3$He in the presence of $O_2$" Phys. Rev. A, 52, pp. 862–865 (1995).

Sauer et al., "Laser Polarized Liquid Xenon", *Chem. Phys. Lett.*, vol. 277, pp. 153–158 (1997).

Schearer, Optical Pumping of Neon $^3P_2$ Metastable Atoms, *Phys Rev.*, 180:83 (1969).

Zeng et al., "Experimental determination of the rate constants for spin exchange between optically pumped K, Rb, and Cs atoms and $^{129}$Xe nuclei in alkali–metal—noble–gas van der Waals molecules", *Physical Review A.*, vol. 31, pp. 260–278 (1985).

Brochure, Jensen Inert Products, Gas Sampling Bags, *jensen@jenseninert.com* (copyright 1997).

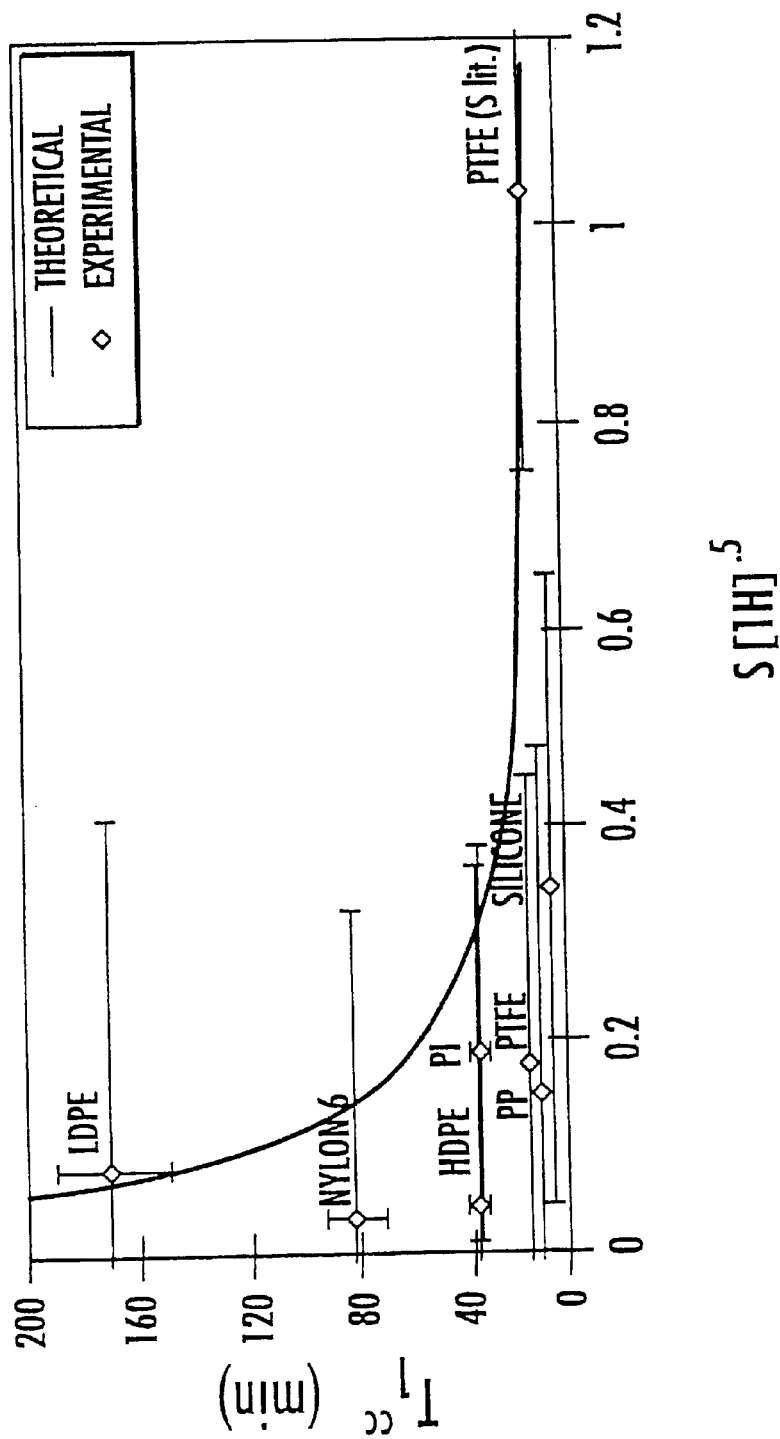

EXPERIMENTAL RESULTS

| MATERIAL | DATE | $T_{1c}$ min | ERROR $T_{1c}$ min | $T_{1p}$ min | ERROR $T_{1p}$ min | RELAXIVITY cm/min | ERROR RELAXIVITY cm/min | $T_1^{cc}$ min | ERROR $T_1^{cc}$ min |
|---|---|---|---|---|---|---|---|---|---|
| XENON | | | | | | | | | |
| POLYETHYLENE (LDPE) | 11.18.97 | 102 | 7.32 | 31.7 | 1.23 | 0.0370 | 0.00391 | 5.59 | 0.59 |
| POLYETHYLENE (HDPE) | 11.18.97 | 113 | 4.96 | 33.2 | 2.18 | 0.0362 | 0.00246 | 5.71 | 0.39 |
| POLYPROPYLENE (PP) | 11.20.97 | 123 | 6.18 | 25.1 | 1.35 | 0.0540 | 0.00349 | 3.83 | 0.25 |
| POLYTETRAFLUOROETHYLENE (PTFE) | 11.25.97 | 107 | 3.67 | 41.7 | 2.12 | 0.0249 | 0.00162 | 8.30 | 0.54 |
| POLYAMIDE - NYLON 6 | 11.25.97 | 118 | 6.96 | 68.6 | 2.55 | 0.0104 | 0.00156 | 19.91 | 2.99 |
| SILICONE ELASTOMER | 12.17.97 | 118 | 2.58 | 5.23 | 0.299 | 0.3112 | 0.00717 | 0.67 | 0.02 |
| POLYIMIDE (PI) | 12.18.97 | 126 | 5.98 | 49.1 | 1.33 | 0.0212 | 0.00169 | 9.78 | 0.78 |
| HELIUM | | | | | | | | | |
| POLYETHYLENE (LDPE) | 3.31.98 | 700 | 28.1 | 470 | 5.16 | 0.0012 | 0.00015 | 170.80 | 21.22 |
| POLYETHYLENE (HDPE) | 5.10.98 | 681 | 45.98 | 213.4 | 2.9 | 0.0056 | 0.00055 | 37.11 | 3.66 |
| POLYPROPYLENE (PP) | 5.4.98 | 681 | 45.98 | 75.2 | 0.5 | 0.0205 | 0.00156 | 10.09 | 0.77 |
| POLYTETRAFLUOROETHYLENE (PTFE) | 4.3.98 | 700 | 28.1 | 98.7 | 3.28 | 0.0151 | 0.00071 | 13.72 | 0.65 |
| POLYAMIDE - NYLON 6 | 5.11.98 | 681 | 45.98 | 342.3 | 2.3 | 0.0025 | 0.00034 | 82.18 | 11.17 |
| SILICONE ELASTOMER | 3.18.98 | 700 | 28.1 | 41.1 | 1.01 | 0.0397 | 0.00169 | 5.21 | 0.22 |
| POLYIMIDE (PI) | 5.10.98 | 681 | 45.98 | 217.1 | 2.7 | 0.0054 | 0.00054 | 38.05 | 3.78 |

FIG. 5.

PREDICTED RESULTS

| MATERIAL | S (MEASURED) | S (LITERATURE) | [1H] mol/L | D₂ cm²/s | $T_{1\rho}$ s | RELAXIVITY cm/min | $T_1^{cc}$ min | LENGTH/SCALE μm |
|---|---|---|---|---|---|---|---|---|
| XENON | | | | | | | | |
| POLYETHYLENE (LDPE) | 0.683 | 0.5896 | 131.43 | 6.90E-08 | 0.065 | 0.0421 | 4.91 | 0.67 |
| POLYETHYLENE (HDPE) | 0.424 | - | 135.71 | - | - | 0.0266 | 7.79 | - |
| POLYPROPYLENE (PP) | 0.682 | - | 128.57 | - | - | 0.0416 | 4.98 | - |
| POLYTETRAFLUOROETHYLENE (PTFE) | 0.726 | 0.7496 | 88.00 | 4.00E-09 | 0.006 | 0.0366 | 5.65 | 0.05 |
| POLYAMIDE - NYLON 6 | 0.310 | - | 98.74 | - | - | 0.0166 | 12.49 | - |
| SILICONE ELASTOMER | 1.930 | 3.9912 | 105.41 | 4.80E-06 | 5.666 | 0.1066 | 1.94 | 52.15 |
| POLYIMIDE (PI) | 4.200 | - | 37.17 | - | - | 0.1377 | 1.50 | - |
| HELIUM | | | | | | | | |
| POLYETHYLENE (LDPE) | 0.0069 | 0.0055 | 131.43 | 6.80E-06 | 0.601 | 0.0014 | 148.68 | 20.22 |
| POLYETHYLENE (HDPE) | 0.0035 | 0.0028 | 135.71 | 3.07E-06 | 0.263 | 0.0007 | 288.45 | 8.98 |
| POLYPROPYLENE (PP) | 0.0130 | 0.0001 | 128.57 | 1.95E-05 | 1.763 | 0.0026 | 79.79 | 58.63 |
| POLYTETRAFLUOROETHYLENE (PTFE) | 0.0190 | 0.1104 | 88.00 | 8.11E-07 | 0.126 | 0.0029 | 71.57 | 3.20 |
| POLYAMIDE - NYLON 6 | 0.0030 | 0.0043 | 98.74 | - | - | 0.0005 | 394.53 | - |
| SILICONE ELASTOMER | 0.0340 | 0.0430 | 105.41 | 4.10E-05 | 4.521 | 0.0061 | 33.69 | 136.14 |
| POLYIMIDE (PI) | 0.0310 | - | 37.17 | - | - | 0.0033 | 62.23 | - |

FIG. 6.

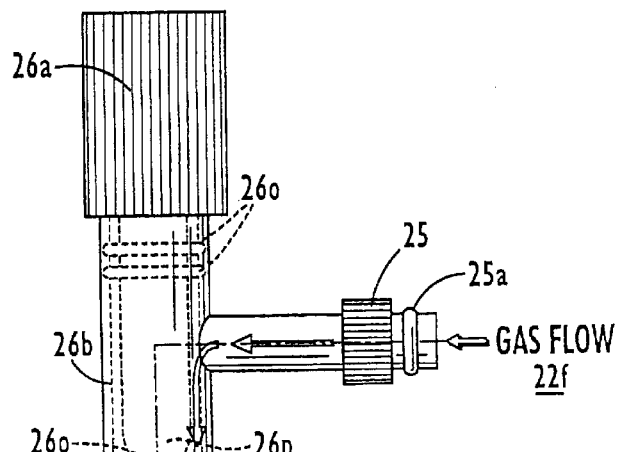
FIG. 9.
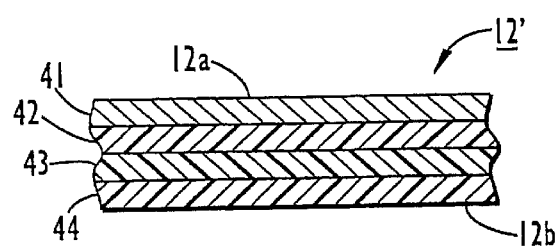
FIG. 10.
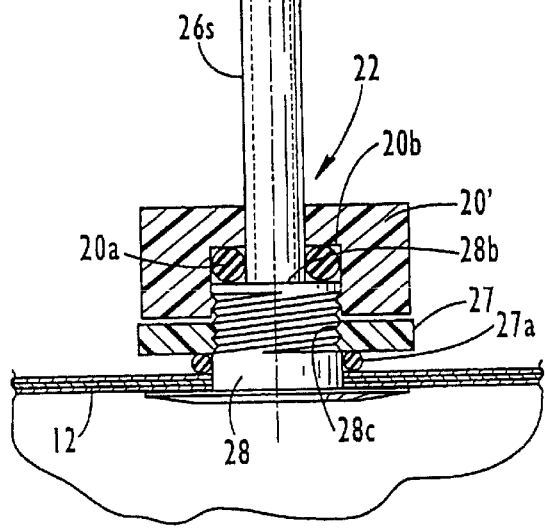
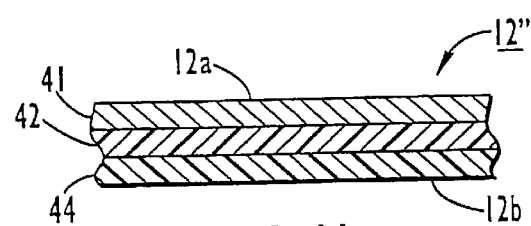
FIG. 11.
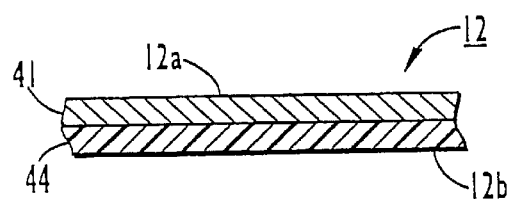
FIG. 12.

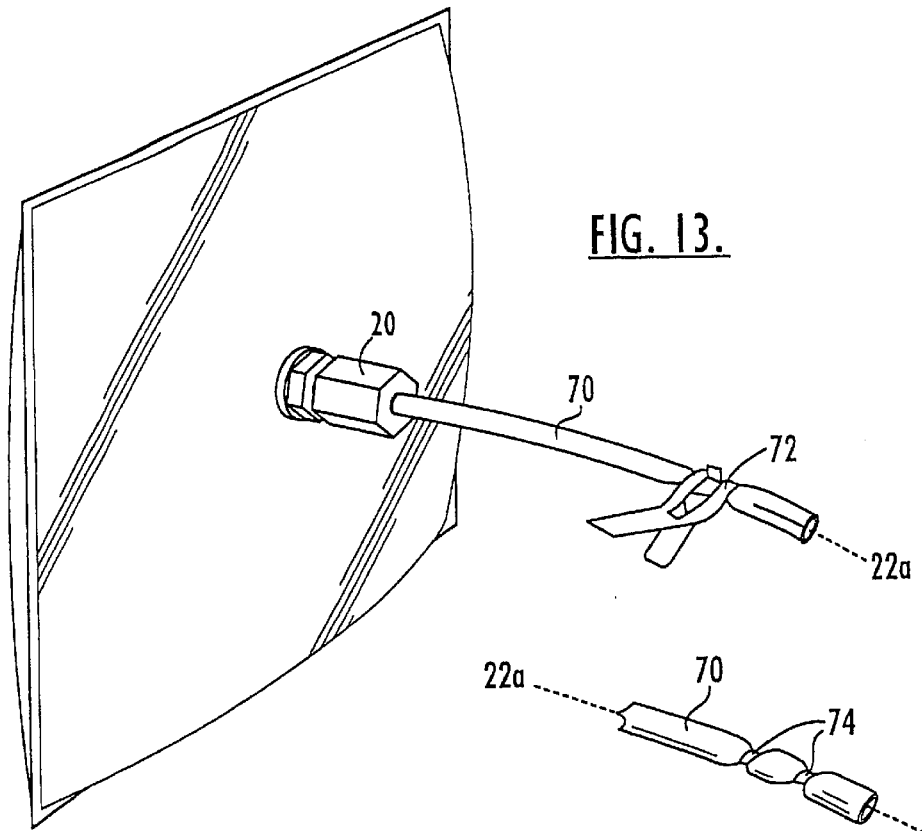
FIG. 13.
FIG. 14.
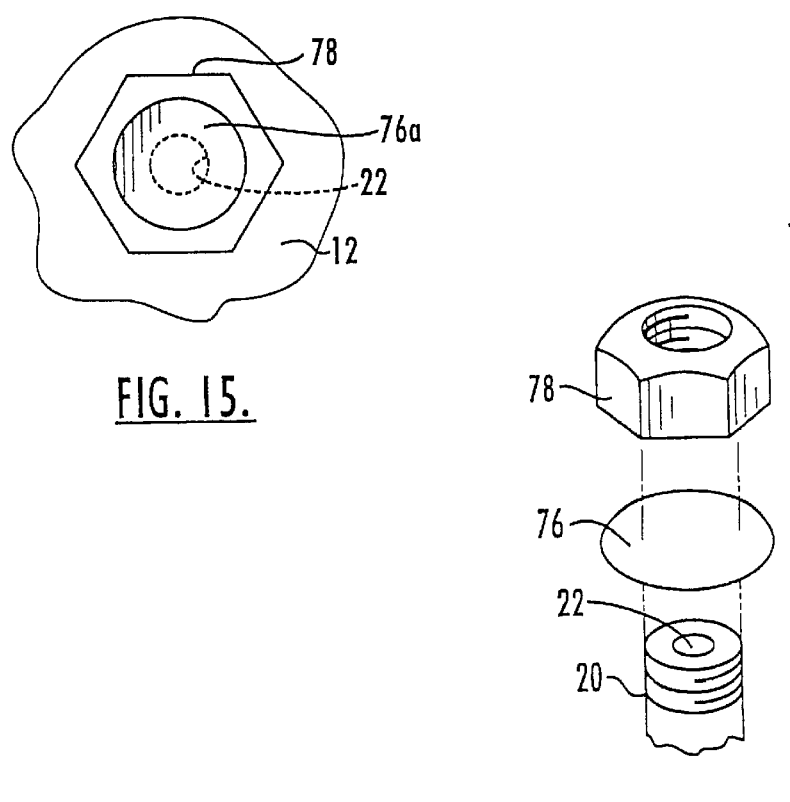
FIG. 15.
FIG. 15A.

CONTAINERS FOR HYPERPOLARIZED GASES AND ASSOCIATED METHODS

This invention was made with Government support under AFOSR Grant No. F41624-97-C-9001 and NIH Grant No. 1 R43 HL59022-01. The United States Government has certain rights in this invention.

FIELD OF THE INVENTION

The present invention relates to processing, storage, transport and delivery containers for hyperpolarized noble gases.

BACKGROUND OF THE INVENTION

Conventionally, Magnetic Resonance Imaging ("MRI") has been used to produce images by exciting the nuclei of hydrogen molecules (present in water protons) in the human body. However, it has recently been discovered that polarized noble gases can produce improved images of certain areas and regions of the body which have heretofore produced less than satisfactory images in this modality. Polarized Helium 3 ("$^3$He") and Xenon-129 ("$^{129}$Xe") have been found to be particularly suited for this purpose. Unfortunately, as will be discussed further below, the polarized state of the gases are sensitive to handling and environmental conditions and, undesirably, can decay from the polarized state relatively quickly.

Hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images of the substance in the body. See U.S. Pat. No. 5,545,396 to Albert et al., the disclosure of which is hereby incorporated herein by reference as if recited in full herein.

In order to produce the hyperpolarized gas, the noble gas is typically blended with optically pumped alkali metal vapors such as rubidium ("Rb"). These optically pumped metal vapors collide with the nuclei of the noble gas and hyperpolarize the noble gas through a phenomenon known as "spin-exchange". The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange".

After the spin-exchange has been completed, the hyperpolarized gas is separated from the alkali metal prior to introduction into a patient to form a non-toxic or sterile composition. Unfortunately, during and after collection, the hyperpolarized gas can deteriorate or decay (lose its hyperpolarized state) relatively quickly and therefore must be handled, collected, transported, and stored carefully. The "$T_1$" decay constant associated with the hyperpolarized gas' longitudinal relaxation time is often used to describe the length of time it takes a gas sample to depolarize in a given container. The handling of the hyperpolarized gas is critical, because of the sensitivity of the hyperpolarized state to environmental and handling factors and the potential for undesirable decay of the gas from its hyperpolarized state prior to the planned end use, i.e., delivery to a patient. Processing, transporting, and storing the hyperpolarized gases—as well as delivery of the gas to the patient or end user—can expose the hyperpolarized gases to various relaxation mechanisms such as magnetic gradients, ambient and contact impurities, and the like.

Typically, hyperpolarized gases such as $^{129}$Xe have been collected in relatively pristine environments and transported in specialty glass containers such as rigid Pyrex™ containers. Flyperpolarized gas such as $^3$He has also been transported in Tedlar™ bags. Unfortunately, these conventional transport containers have produced relatively short relaxation times or can require relatively complex gas extraction systems which often leaves relatively large residual amounts of the gas in the container at the end use point.

One way of inhibiting the decay of the hyperpolarized state is presented in U.S. Pat. No. 5,612,103 to Driehuys et al. entitled Coatings for Production of Hyperpolarized Noble Gases. Generally stated, this patent describes the use of a modified polymer as a surface coating on physical systems (such as a Pyrex™ container) which contact the hyperpolarized gas to inhibit the decaying effect of the surface of the collection chamber or storage unit. However, there remains a need to address and refine dominant and sub-dominant relaxation mechanisms and to decrease the amount of physical systems required to deliver the hyperpolarized gas to the desired subject. Minimizing the effect of one or more of these factors can increase the life of the product by increasing the duration of the hyperpolarized state. Such an increase is desired so that the hyperpolarized product can retain sufficient polarization to allow effective imaging at delivery when transported over longer transport distances and for longer time periods from the initial polarization than has been viable previously.

OBJECTS AND SUMMARY OF THE INVENTION

In view of the foregoing, it is an object of the present invention to process and collect hyperpolarized gas in improved containers which are configured to inhibit de-polarization in the collected polarized gas.

It is another object of the present invention to provide an improved container which can be configured to act as both a transport container and a delivery mechanism to reduce the amount of handling or physical interaction required to deliver the hyperpolarized gas to a subject.

It is a further object of the present invention to provide an improved, relatively non-complex and economical container which can prolong the polarization life of the gas in a container and reduce the amount of polarization lost during transport and delivery.

It is yet another object of the invention to provide methods, surface materials and containers which will minimize the de-polarizing effects of the hyperpolarized state of the gas (especially $^3$He) attributed to one or more of paramagnetic impurities, oxygen exposure, stray magnetic fields, and surface relaxation.

It is an additional object of the present invention to provide a method to determine the gas solubility in polymers or liquids with respect to hyperpolarized $^{129}$Xe or $^3$He.

These and other objects are satisfied by the present invention which is directed to a resilient container and/or gas contact surfaces which are configured to reduce surface or contact depolarization by forming an inner contact surface of a first material of a predetermined thickness which acts to minimize the associated surface or contact depolarization. In particular, a first aspect of the invention is directed to a container for receiving a quantity of hyperpolarized gas. The container includes at least one wall comprising inner and outer layers configured to define an enclosed chamber for holding a quantity of hyperpolarized gas. The inner layer has a predetermined thickness and an associated relaxivity value which inhibits contact induced polarization loss of the hyperpolarized gas, and the outer layer defines an oxygen shield overlying the inner layer and is configured to minimize the migration of oxygen into the container. Of course, the two layers can be integrated into one if the material chosen acts both as a polarization friendly contact surface and which is also resistant to the introduction of oxygen molecules into the chamber of the container. The container also includes a quantity of hyperpolarized noble gas and a port attached to the wall in fluid communication with the chamber for capturing and releasing the hyperpolarized gas therethrough. Preferably, the inner layer thickness ("$L_{th}$") is at least as thick as the polarization decay length scale ("$L_p$") which can be determined by the equation:

$$L_p = \sqrt{T_p D_p}$$

where $T_p$ is the noble gas nuclear spin relaxation time in the polymer and $D_p$ is the noble gas diffusion coefficient in the polymer.

Advantageously, using a contact surface which has a thickness which is larger than the polarization decay length scale can minimize or even prevent the hyperpolarized gas from sampling the substrate (the material underlying the first layer). Indeed, for hyperpolarized gases which can have a high diffusion constant (such as $^3$He), surfaces with polymer coatings substantially thinner than the polarization decay length scale can have a more detrimental effect on the polarization than surfaces having no such coating at all. This is because the polarized gas can be retained within the underlying material and interact with the underlying or substrate material for a longer time, potentially causing more depolarization than if the thin coating is not present.

In a preferred embodiment, the container of the instant invention is configured to receive hyperpolarized $^3$He and the inner layer is at least 16–20 microns thick. In another preferred embodiment, the container is an expandable polymer bag. Preferably, the polymer bag includes a metallized coating positioned over the polymer which suppresses the migration of oxygen into the polymer and ultimately into the polarized gas holding chamber. Advantageously, the captured hyperpolarized gas can be delivered to the inhalation interface of a subject by exerting pressure on the bag to collapse the bag and cause the gases to exit the chamber. This, in turn, removes the requirement for a supplemental delivery mechanism. It is additionally preferred that the container use seals such as O-rings which are substantially free of paramagnetic impurities. The proximate position of the seal with the hyperpolarized gas can make this component a dominant factor in the depolarization of the gas. Accordingly, it is preferred that the seal or O-ring be formed from substantially pure polyethylene or polyolefins such as ethylene, propylene, copolymers and blends thereof. Of course, fillers which are friendly to the hyperpolarization can be used (such as substantially pure carbon black and the like). Alternatively, the O-ring or seal can be coated with a surface material such as LDPE or deuterated HDPE or other low-relaxivity property material.

Similar to the preferred embodiment discussed above, another embodiment of the present invention is a resilient container for holding hyperpolarized gas. The container comprises a first layer of a first material configured to define an expandable chamber to hold a quantity of hyperpolarized gas therein. Preferably, the first layer has a predetermined thickness sufficient to inhibit surface or contact depolarization of the hyperpolarized gas held therein wherein the first layer material has a relaxivity value "Y". Also preferably, the relaxivity value "Y" is less than about 0.0012 cm/min for $^3$He and less than about 0.01 cm/min for $^{29}$Xe. The container also includes a second layer of a second material positioned such that the first layer is between the second layer and the chamber, wherein the first and second layers are concurrently responsive to the application of pressure and one of the first and second layers acts as an oxygen shield to suppress oxygen permeability into the chamber. Additional layers of materials can be positioned intermediate the first layer and the second layer. In one preferred embodiment, hyperpolarized gas has a low relaxivity value in the first layer material and the second layer preferably comprises a material which can shield the migration of the oxygen into the first layer. In another preferred embodiment, the resilient container has a first layer formed of a metal film (which can act both as an oxygen shield and contact surface). In this embodiment, it is preferred that the relaxivity values are less than about 0.0023 and 0.0008 for $^{129}$Xe and $^3$He respectively. Stated differently, it is preferred that the hyperpolarized gas have a high mobility on the metal surface or small absorption energy relative to the metal contact surface such that the $T_1$ of the gas in the container approaches >50% of its theoretical limit.

Another aspect of the invention is a method of inhibiting the depolarization of a quantity of captured hyperpolarized gas. The internal surface of a chamber configured to receive a quantity of hyperpolarized gas is coated or formed with a predetermined thickness of a material having low relaxivity value for the hyperpolarized gas. The coating thickness is at least as thick as the polarization decay length scale ("$L_p$") expressed by the equation stated above. Preferably, the coating or material layer thickness is greater than a plurality of the polarization decay length scale. Alternately, in another embodiment, the internal surface of a resilient container is formed from a high puritynon-magnetic metal film.

An additional aspect of the present invention is directed to a method for storing, transporting and delivering hyperpolarized gas to a target. The method includes introducing a quantity of hyperpolarized gas into a container. The container has a wall comprising a material resistant to the transport of oxygen into the container. Preferably, the container is expanded to capture the quantity of hyperpolarized gas. The container is sealed to contain the hyperpolarized gas therein. The container is transported to a site remote from the hyperpolarization site. The hyperpolarized gas is delivered to a target by compressing the chamber and thereby forcing the hyperpolarized gas to exit therefrom. Preferably, in order to maintain the hyperpolarized state, the container is substantially continuously, from the time of polarization to the delivery, either shielded or exposed to a proximately maintained magnetic field to protect it from undesired external magnetic fields. Further preferably, the container can be re-used (after re-sterilization) to ship additional quantities of hyperpolarized gases.

Another aspect of the present invention is a method of inhibiting the depolarization of hyperpolarized gas in a container configured to collect a quantity of hyperpolarized gas. The method includes forming a seal from a material which is substantially free of paramagnetic impurities to inhibit the depolarization effect attributed to its proximate location to the hyperpolarized gas in the container.

Similarly, a further aspect of the present invention is a valve for containers configured to releasably capture hyperpolarized gases. The valve comprises an entry port configured to engage with a hyperpolarized gas chamber. The entry port has a passage in fluid communication with the container. The valve also includes a valve member having open and closed positions and a seal operably associated with the valve and the container, wherein the seal is proximate to the hyperpolarized gas, and wherein the seal is formed from a material which is substantially free of paramagnetic impurities or which is coated with a material which has a low relaxivity value relative to the hyperpolarized gas.

An additional aspect of the present invention is a method for preparing an expandable storage container for receiving a quantity of hyperpolarized gas. The method includes providing a quantity of purge gas into the hyperpolarized gas container and expanding the hyperpolarized gas container. The container is then collapsed to remove the purge gas. The oxygen in the container walls is outgassed by decreasing the oxygen partial pressure in the container thereby causing a substantial amount of the oxygen trapped in the walls of the container to migrate into the chamber of the container in the gas phase where it can be removed. Preferably, after the outgassing step, the container is filled with a quantity of storage gas such as nitrogen. The gas is introduced into the container at a pressure which minimizes the pressure differential across the walls of the container to minimize further outgassing of the container. Preferably, the container is then stored for future use (temporally spaced apart from the time of preconditioning). The storage nitrogen and outgassed oxygen are removed from the container before filling with a quantity of hyperpolarized gas. Preferably, after removal from storage and prior to use, the nitrogen is removed by evacuating the container before filling with a quantity of hyperpolarized gas.

Yet another aspect of the present invention is directed to a method for shielding the hyperpolarized noble gas from stray magnetic fields. Preferably, the method includes shifting the normal frequency associated with the hyperpolarized gas to a frequency substantially outside the bandwidth of prevalent stray oscillating fields found in vehicles and other sources.

Another aspect of the present invention is directed to a method for determining the hyperpolarized gas ($^{129}$Xe or $^3$He) solubility in a (unknown) polymer or a particular fluid. The method includes introducing a first quantity of hyperpolarized noble gas into a container having a known free volume and measuring a first relaxation time of the hyperpolarized gas in the container. A sample of desired material is positioned into the container and a second quantity of hyperpolarized noble gas is introduced into the container. A second relaxation time of the second hyperpolarized gas is measured in the container with the sample material. The gas solubility of the sample is determined based on the difference between the two measured relaxation times. The material sample can be a structurally rigid sample (geometrically fixed) with a known geometric surface area/volume which is inserted into the free volume of the chamber or container. Alternatively, the material sample can be a liquid which partially fills chamber.

Advantageously, the methods and containers of the present invention can improve the relaxation time (lengthen $T_1$) of the hyperpolarized gas by contacting the hyperpolarized gas with a hyperpolarized contact surface having a specified depth of a low-relaxivity value material relative to the hyperpolarized noble gas. Further advantageously, the container itself can be configured to provide the contact surface by forming the container out of a resilient material such as a polymer bag. This configuration provides a relatively non-complex container which can conveniently be re-used. Alternatively, the internal surface of a container can be formed from a high purity metal providing the contact surface. Additionally, the collapsible containers can be used to deliver the gas into the patient interface without the need for additional delivery vehicles/equipment. This can reduce the exposure, handling, and physical manipulation of the hyperpolarized gas which, in turn, can increase the polarization life of the hyperpolarized gas. Resilient containers with high purity contact surfaces can be extremely advantageous for both $^{129}$Xe and $^3$He as well as other hyperpolarized gases; however, the expandable polymer container and coatings/layers are especially suited for hyperpolarized $^3$He. Further, the instant invention can shield the hyperpolarized gas in a shipping container from stray magnetic fields, especially deleterious oscillating fields which can easily dominate other relaxation mechanisms.

Additionally, the present invention can be used to determine the gas solubility in polymers or fluids which in the past has proven difficult and sometimes inaccurate, especially for helium.

Advantageously, the present invention now provides a way to model the predictive behavior of surface materials and is particularly suited to determining the relaxation properties of polymers used as contact materials in physical systems used to collect, process, or transport hyperpolarized gases. For example, the present invention successfully provides relaxation properties of various materials (measured and/or calculated). These relaxation values can be used to determine the relaxation time ($T_1$) of hyperpolarized gas in containers corresponding to the solubility of the gas, the surface area of the contact material, and the free gas volume in the container. This information can be advantageously used to extend the hyperpolarized life of the gas in containers over those which were previously achievable in high-volume production systems.

The foregoing and other objects and aspects of the present invention are explained in detail herein.

BRIEF DESCRIPTION OF THE DRAWINGS

FIG. 4 is a graph similar to FIG. 3 showing the results of standardized relaxation times for $^3$He.

FIG. 5 is a detailed chart of predicted material values for Xenon and Helium.

FIG. 6 is a detailed chart of experimental material values for Xenon and Helium.

FIG. 9 is a sectional view of the container shown in FIG. 7 according to one embodiment of the present invention.

FIG. 10 is an enlarged partial cutaway section view of the container wall according to another embodiment of the present invention.

FIG. 11 is an enlarged partial cutaway section view of an additional embodiment of a container wall according to the present invention.

FIG. 12 is an enlarged partial cutaway section view of yet another embodiment of a container wall according to the present invention.

FIG. 13 is a perspective view of a preferred embodiment of a container with a seal according to the present invention.

FIG. 14 illustrates the container of FIG. 13 with an alternative external seal according to an additional embodiment of the present invention.

FIG. 15 illustrates another container with an alternative seal arrangement according to another embodiment of the present invention.

FIG. 15A is an exploded view of the container shown in FIG. 15.

DETAILED DESCRIPTION OF THE PREFERRED EMBODIMENTS

Figure 1:
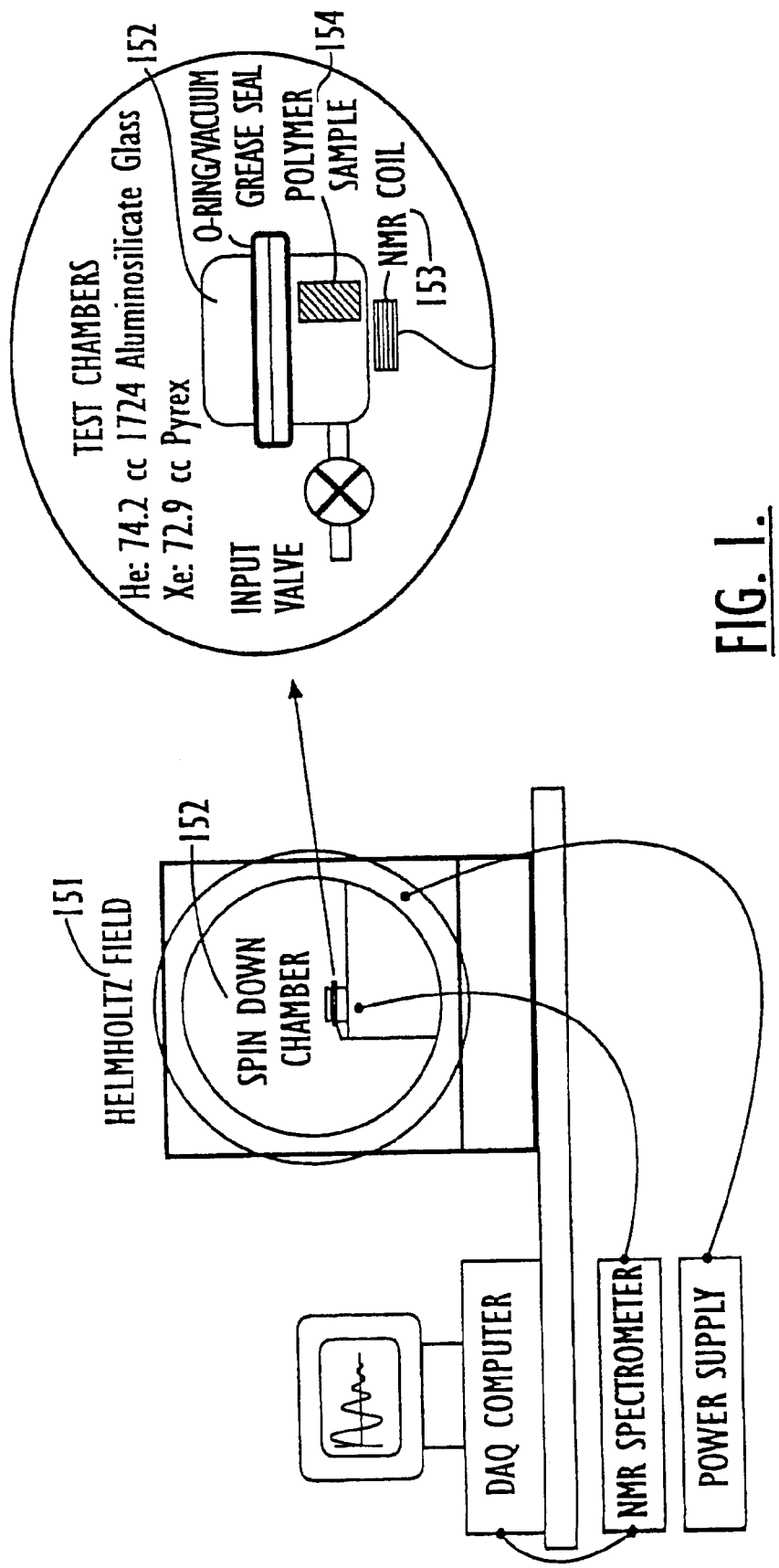
FIG. 1 is a schematic diagram of a spin-down station used to measure relaxation times according to one aspect of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers and regions may be exaggerated for clarity. For ease of discussion, the term "hyperpolarized gas" will be used to describe a hyperpolarized gas alone, or a hyperpolarized gas which contacts or combines with one or more other components whether gaseous, liquid, or solid. Thus, the hyperpolarized gas described herein can be a hyperpolarized gas composition/mixture (non-toxic such that it is suitable for in vivo introduction) such that the hyperpolarized noble gas can be combined with other noble gases and/or other inert or active components. Also, as used herein, the term "hyperpolarized gas" can include a product where the hyperpolarized gas is dissolved into another liquid (such as a carrier) or processed such that it transforms into a substantially liquid state, i.e., "a liquid polarized gas". Thus, although the term includes the word "gas", this word is used to name and descriptively track the gas produced via a hyperpolarizer to obtain a polarized "gas" product. In summary, as used herein, the term "gas" has been used in certain places to descriptively indicate a hyperpolarized noble gas which can include one or more components and which may be present in one or more physical forms.

Preferred hyperpolarized noble gases (either alone or in combination) are listed in Table I. This list is intended to be illustrative and non-limiting.

TABLE I

Hyperpolarizable Noble Gases

| Isotope | Natural Abundance (%) | Nuclear Spin |
|---|---|---|
| $^3$He | ~$10^{-6}$ | 1/2 |
| $^{21}$Ne | 0.27 | 3/2 |
| $^{83}$Kr | 11.5 | 9/2 |
| $^{129}$Xe | 26.4 | 1/2 |
| $^{131}$Xe | 21.2 | 3/2 |

Hyperpolarization

Various techniques have been employed to polarize, accumulate and capture polarized gases. For example, U.S. Pat. No. 5,642,625 to Cates et al. describes a high volume hyperpolarizer for spin polarized noble gas and U.S. patent application Ser. No. 08/622,865 to Cates et al. describes a cryogenic accumulator for spin-polarized $^{129}$Xe. The disclosures of this patent and application are hereby incorporated herein by reference as if recited in full herein. As used herein, the terms "hyperpolarize" and "polarize" are used interchangeably and mean to artificially enhance the polarization of certain noble gas nuclei over the natural or equilibrium levels. Such an increase is desirable because it allows stronger imaging signals corresponding to better MRI images of the substance and a targeted area of the body. As is known by those of skill in the art, hyperpolarization can be induced by spin-exchange with an optically pumped alkali-metal vapor or alternatively by metastability exchange. See U.S. Pat. No. 5,545,396 to Albert et al. The alkali metals capable of acting as spin exchange partners in optically pumped systems include any of the alkali metals. Preferred alkali metals for this hyperpolarization technique include Sodium-23, Potassium-39, Rubidium-85, Rubidium-87, and Cesium-133. Alkali metal isotopes, and their relative abundance and nuclear spins are listed in Table II, below. This list is intended to be illustrative and non-limiting.

TABLE II

Alkali Metals Capable of Spin Exchange

| Isotope | Natural Abundance (%) | Nuclear Spin |
|---|---|---|
| $^{23}$Na | 100 | 3/2 |
| $^{39}$K | 93.3 | 3/2 |
| $^{85}$Rb | 72.2 | 5/2 |
| $^{87}$Rb | 27.8 | 3/2 |
| $^{133}$Cs | 100 | 7/2 |

Alternatively, the noble gas may be hyperpolarized using metastability exchange. (See e.g., Schearer L D, *Phys Rev*, 180:83 (1969); Laloe F, Nacher P J, Leduc M, and Schearer L D, AIP ConfProx #131 (Workshop on Polarized $^3$He Beams and Targets) (1984)). The technique of metastability exchange involves direct optical pumping of, for example, $^3$He without need for an alkali metal intermediary. The method of metastability exchange usually involves the excitation of ground state $^3$He atoms ($1^1S_0$) to a metastable state ($2^3S_1$) by weak radio frequency discharge. The $2^3S_1$ atoms are then optically pumped using circularly polarized light having a wavelength of 1.08 μm in the case of $^3$He. The light drives transitions up to the $2^3P$ states, producing high polarizations in the metastable state to which the $2^3S$ atoms then decay. The polarization of the $2^3S_1$ states is rapidly transferred to the ground state through metastability exchange collisions between metastable and ground state atoms. Metastability exchange optical pumping will work in the same low magnetic fields in which spin exchange pumping works. Similar polarizations are achievable, but generally at lower pressures, e.g., about 0–10 Torr.

Generally described, for spin-exchange optically pumped systems, a gas mixture is introduced into the hyperpolarizer apparatus upstream of the polarization chamber. Most xenon gas mixtures include a buffer gas as well as a lean amount of the gas targeted for hyperpolarization and is preferably produced in a continuous flow system. For example, for producing hyperpolarized $^{129}$Xe, the pre-mixed gas mixture is about 95–98% He, about 5% or less $^{129}$Xe, and about 1% $N_2$. In contrast, for producing hyperpolarized $^3$He, a mixture of 99.25% $^3$He and 0.75% $N_2$ is pressurized to 8 atm or more and heated and exposed to the optical laser light source in a batch mode system. In any event, once the hyperpolarized gas exits the pumping chamber it is directed to a collection or accumulation container.

A 5–20 Gauss alignment field is typically provided for the optical pumping of Rb for both $^{129}$Xe and $^3$He polarization. The hyperpolarized gas is collected (as well as stored, transported, and preferably delivered) in the presence of a magnetic field. It is preferred for solid (frozen) $^{129}$Xe that the field be on the order of at least 500 Gauss, and typically about 2 kilo Gauss, although higher fields can be used. Lower fields can potentially undesirably increase the relaxation rate or decrease the relaxation time of the polarized gas. As regards $^3$He, the magnetic field is preferably on the order of at least 5–30 gauss although, again, higher (homogeneous) fields can be used. The magnetic field can be provided by electrical or permanent magnets. In one embodiment, the magnetic field is provided by a plurality of permanent magnets positioned about a magnetic yoke which is positioned adjacent the collected hyperpolarized gas. Preferably, the magnetic field is homogeneously maintained around the hyperpolarized gas to minimize field induced degradation.

Polarized Gas Relaxation Processes

Once hyperpolarized, there is a theoretical upper limit on the relaxation time ($T_1$) of the polarized gas based on the collisional relaxation explained by fundamental physics, i.e., the time it takes for a give sample to decay or depolarize due to collisions of the hyperpolarized gas atoms with each other absent other depolarizing factors. For example, $^3$He atoms relax through a dipole-dipole interaction during $^3$He—$^3$He collisions, while $^{129}$Xe atoms relax through N·I spin rotation interaction (where N is the molecular angular momentum and I designates nuclear spin rotation) during $^{129}$Xe—$^{129}$Xe collisions. Stated differently, the angular momentum charge associated with flipping a nuclear spin over is conserved by being taken up by the rotational angular momentum of the colliding atoms. In any event, because both processes occur during noble gas-noble gas collisions, both resulting relaxation rates are directly proportional to gas pressure ($T_1$ is inversely proportional to pressure). Thus, at one atmosphere, the theoretical relaxation time ($T_1$) of $^3$He is about 744–760 hours, while for $^{129}$Xe the corresponding relaxation time is about 56 hours. See Newbury et al., Gaseous $^3$He—$^3$He Magnetic Dipolar Spin Relaxation, 48 Phys. Rev. A., No. 6, p. 4411 (1993); Hunt et al., Nuclear Magnetic Resonance of $^{129}$Xe in Natural Xenon, 130 Phys Rev. p. 2302 (1963). Unfortunately, other relaxation processes prevent the realization of these theoretical relaxation times. For example, the collisions of gaseous $^{129}$Xe and $^3$He with container walls ("surface relaxation") have historically dominated most relaxation processes. For $^3$He, most of the known longer relaxation times have been achieved in special glass containers having a low permeability to helium. In the past, a fundamental understanding of surface relaxation mechanisms has been elusive which has made the predictability of the associated $T_1$ difficult.

U.S. Pat. No. 5,612,103 to Driehuys et al. describes using coatings to inhibit the surface-induced nuclear spin relaxation of hyperpolarized noble gases, especially $^{129}$Xe. The contents of this patent are hereby incorporated by reference as if recited in full herein. Driehuys et al. recognized that nuclear spin relaxation of $^{129}$Xe on a polydimethoylsiloxane ("PDMS") surface coating can be dominated by dipolar coupling of the $^{129}$Xe nuclear spin to the protons in the polymer matrix. Thus, it was demonstrated that paramagnetic contaminants (such as the presence of paramagnetic molecules like oxygen) were not the dominant relaxation mechanism in that system because the inter-nuclear dipole-dipole relaxation was found to dominate the system under investigation. This was because $^{129}$Xe substantially dissolved into the particular polymer matrix (PDMS) under investigation. See Bastiaan Driehuys et al., Surface Relaxation Mechanisms of Laser-Polarized $^{129}$Xe, 74 Phys. Rev. Lett., No. 24, pp. 943–4946 (1995).

One aspect of the instant invention now provides a more detailed understanding of noble gas depolarization on polymer surfaces. Indeed, as will be explained further below, noble gas solubility in large numbers of polymer systems (not just PDMS) can cause inter-nuclear dipole-dipole relaxation to dominate the polarization decay rate. Notably, this insight now indicates that polymers can be especially effective for the suppression of $^3$He relaxation. In addition, a predictive explanation of noble gas relaxation on polymer surfaces is discussed below. Advantageously, it is now possible to calculate and measure the relaxation properties of various materials. This information can be advantageously used with other parameters such as free gas volume and surface area of containers to provide more effective and advantageous surface configurations and material characteristics which can facilitate, preserve, and further improve the polarization life of the noble gas. This is especially useful in providing containers which can yield reliable, repeatable, and predictable high-volume polarization production performance which in the past has been difficult to achieve outside the pristine conditions of a small production laboratory.

Generally stated, magnetic interactions can alter the time constant of relaxation, referred to as the longitudinal relaxation time ($T_1$), and typically occur when different atoms encounter one another. In the case of hyperpolarized noble gases held in containers, the nuclear magnetic moments of the gas atoms interact with the surface materials to return the gas to the equilibrium or non-hyperpolarized state. The strength of the magnetic moment can be a determinative factor in determining the relaxation rate associated with the surface material. Since different atoms and molecules have different magnetic moments, relaxation rates are material specific.

Relaxivity of Materials

In order to compare the characteristic information of certain materials concerning their respective relaxing effects on hyperpolarized noble gases, the term "relaxivity" is used. As used herein, the term "relaxivity" ("Y") is used to describe a material property associated with the rate of depolarization ("$1/T_1$") of the hyperpolarized gas sample. For a container having a chamber volume "Vc" capable of holding a quantity of hyperpolarized gas and for a material sample with a surface area "A" in the container chamber, each time a polarized gas atom contacts the container surface, it has a probability ("p") of depolarizing. The rate of depolarization ($1/T_1$)of this gas sample in the chamber can then be described by p times the rate at which gas atoms collide with the surface ("R").

$$\frac{1}{T_1} = Rp \quad (2.1)$$

The average surface collision rate (R) per gas atom is known from statistical mechanics, R. Reif, *Fundamentals of statistical and Thermal Physics*, McGraw-Hill (1965):

$$R = \frac{vA}{4V} \quad (2.2)$$

In this equation, "v" is the mean thermal velocity of the gas atoms. For the case of a one cubic centimeter ("1 cc") sphere of $^{129}$Xe the area is $A=4\pi r^2$ and the volume is $V=4\pi r3/3$. Thus, for v=154 m/s, equation (2.2) yields a collision rate $R=800$ s$^{-1}$. In other words, each atom of Xe is contacting the surface of the sphere 800 times in 1 second. Therefore, according to equation (2.1) long $T_1$ times must have a minute probability for depolarization during each collision (p<<1). Substituting equation (2.2) back into equation (2.1) yields:

$$\frac{1}{T_1} = \frac{Avp}{4V} \quad (2.3)$$

Since measurements for this study are performed at room temperature, "v" will not vary. Therefore, the relaxivity term, ("Y") which is defined as Y=vp/4, results in:

$$\frac{1}{T_1} = \frac{A}{V}\Upsilon \quad (2.4)$$

Thus, relaxivity ("Y") is a material property that can describe the depolarizing effect that a specific material has on a hyperpolarized gas sample.

When considering hyperpolarized gas containers, it is important to notice the relationship between the $1/T_1$ and A/V terms in Equation 2.4. Thus, the ratio "A/V" for a sphere with a radius "r", the ratio reduces to 3/r. Therefore, a one liter sphere (1000 cc, r=6.2 cm) has a $T_1$ that is 10 times longer than a sphere with a one cubic centimeter volume (1 cc, r=0.62 cm) made of the same material. Therefore, preferably, in order to improve the $T_1$ of hyperpolarized gas in the containers, the containers are configured and sized to decrease the value of the ratio A/V—i.e., to increase the volume relative to the area of the container, as will be discussed further below.

Determining Relaxivity

Equation 2.4 can be used to calculate relaxivity of the gas if surface relaxation is the only (dominant) depolarizing effect at work. In the case of practical material studies, this is not the case. The surfaces of the test chamber, the chamber seal, and other impurities also contribute to the relaxation of the gas. However, by using the relaxation time differences between hyperpolarized gas in an empty test chamber and the hyperpolarized gas in the chamber containing a material sample positioned to contact the hyperpolarized gas, the characteristic relaxivity of the material can be determined.

Note that the relaxation rates are additive in the following form:

$$\frac{1}{T_1} = \frac{1}{T_1^a} + \frac{1}{T_1^b} + \frac{1}{T_1^c} \ldots \quad (2.5)$$

In general form, $T_1^a$ can represent the relaxation effect of the test chamber surface, $T_b^1$ can represent the effect of the hyperpolarized gas atoms colliding with one another, and so on. Assuming that surface relaxation is the dominant relaxation effect, the relaxation rate can be described by adding the surface effects of the material sample and the test chamber.

$$\frac{1}{T_1} = \frac{A_m \Upsilon_m}{V} + \frac{A_c \Upsilon_c}{V} \quad (2.6)$$

where $A_m$ and $\Upsilon_m$ describes the area and relaxivity respectively of the material sample and $A_c$ and $\Upsilon_c$ correspond to the area and relaxivity of the container or chamber. "V" is the free gas volume in the chamber. In this case, $V=V_c-V_m$, where "$V_c$" is the volume of the chamber and "$V_m$" is the volume of the container occupied by the material sample. In relaxivity studies for new materials (where the material sample is small) the free volume "V" can be reasonably approximated as equal to $V_c$, i.e. $V=V_c$. Substituting back into (2.6):

$$\frac{1}{T_1} = \frac{A_m \Upsilon_m}{V_c} + \frac{A_c \Upsilon_c}{V_c} \quad (2.7)$$

Note that for a chamber without a material sample, this equation reduces to:

$$\frac{1}{T_{1c}} = \frac{A_c \Upsilon_c}{V_c} \quad (2.8)$$

where $T_{1c}$ is the characteristic relaxation rate of the container or empty chamber. Substituting (2.8) into (2.7) yields:

$$\frac{1}{T_1} = \frac{A_m \Upsilon_m}{V_c} + \frac{1}{T_{1c}} \quad (2.9)$$

Solving equation (2.9) gives an expression for the relaxivity $\Upsilon_m$ associated with a specific material sample with a measured $T_1$ in a chamber with known volume and observed $T_{1c}$:

$$\Upsilon_m = \frac{V_c}{A_m}\left(\frac{1}{T_1} - \frac{1}{T_{1c}}\right) \quad (2.10)$$

The relaxivity of a given material can easily be translated back into a more intuitive characteristic relaxation time. One method of comparison, in keeping with past surface relaxation rate studies, is to describe the relaxation rate as if there were a 1 cc spherical cell made of the material in question.

Knowing the volume and surface area of such a cell ($A=4\pi r^2$, $V=4\pi r^3/3$, $r=0.62$ cm) and substituting back into (2.8):

$$T_1^{cc} = \frac{0.207\,\text{cm}}{\Upsilon_c} \quad (2.11)$$

Again, this container geometry is for illustration as it standardizes the relaxation term for comparison with past data. For reference, observed $T_1$ values from $^{129}$Xe studies in the past showed ultra clean Pyrex with a Rb monolayer surface to have an associated $T^{cc}_1=30$ minutes.

Experimental Determination of Relaxivity

The hyperpolarized gas samples were used in a materials testing center known as the Spin Down Station. This apparatus was constructed to test various material samples in a controlled environment. The system consists of a materials testing chamber, a Pulse-NMR Spectrometer, and a Lab View user interface. The flexible system allows various chambers or bags to be cleaned and filled with polarized $^{129}$Xe or $^3$He. The Pulse-NMR system then charts the relaxation of signal from these containers over time.

Equipment Layout

FIG. 1 is a schematic diagram of the Spin Down Station. This apparatus consists of a Helmholtz pair generating a stable Helmholtz magnetic field 151 around the glass test chamber labeled the Spin Down Chamber 152. The signal response frequency (f) is proportional to the applied magnetic field ($B_0$) expressed by the equation ($f=\gamma B_0/2\pi$). This proportionally constant is known as the gyromagnetic ratio ($\gamma_{He}=7400$ s$^{-1}$ G$^{-1}$, $\gamma_{Xe}=26700$ s$^{-1}$ G$^{-1}$). If the applied magnetic field remains constant, the coil must be tuned to switch between the two gases. As an alternative to retuning, the field strength was adjusted to result in the same frequency response for both gases. A current of 1.0 A (7 G field) for $^3$He and 2.5 A (21 G field) for $^{129}$Xe was applied to the Helmholtz pair noted by the Helmholtz field shown in FIG. 1. In the center of Helmholtz field 151 rested one of the two spin down chambers 152 used in these tests. Both chambers were valved to evacuate (base pressure ~30 miliTorr) and fill the chamber with hyperpolarized gas. Each chamber could be opened to insert polymer samples (typically 10 mm×20 mm×1 mm). As shown, the NMR coil 153 rests beneath the chamber in the center of the Helmholtz field 151.

The first spin down chamber was made of Pyrex™ coated with dimethyl dichlorosilane (DMDCS) and used a Teflon™ coated rubber O-ring as the vacuum seal. This chamber had a 110 minute characteristic $T_{1c}$ suitable for observing the surface relaxation effects of various polymer samples 154. Notably, after numerous tests, the $T_{1c}$ would often decrease. A thorough cleaning with high-purity ethanol restored the chamber to the baseline value. Unfortunately, the $T_{1c}$ for the Pyrex™ chamber with $^3$He was not long enough to distinguish good from bad materials for $^3$He. Tests of various glasses in the Pyrex™ spin down chamber showed that a chamber made of 1724 aluminosilicate glass would have a sufficiently long $T_{1c}$ for $^3$He.

The 1724 $^3$He chamber was constructed with a ground seal requiring Apiezon™ vacuum grease. The chamber had a characteristic $T_{1c}$ of 12 hour on average. The Apiezon™ grease used to seal both the chamber and the entry valve caused the chamber $T_{1c}$ to fluctuate significantly more than the Pyrex™ chamber. To restore the chamber to baseline $T_{1c}$ the grease was removed by cleaning the chamber with high-purity Hexane.

Testing Procedure

Using the Spin Down Station, seven polymer samples were tested using hyperpolarized $^{129}$Xe or $^3$He. These polymers were purchased from Goodfellow, Inc., Berwyn, Pa.

| Material | Density | Thickness (mm) ($T_1$ study) | Thickness (mm) (Sorption study) |
|---|---|---|---|
| Polyamide (Nylon 6) | 1.13 | 1 | 0.012* |
| Silicone Elastomer | 1.1–1.3 | 1 | 1 |
| High Density Polyethylene (HDPE) | 0.95 | 1 | 0.01 |
| Low Density Polyethylene (LDPE) | 0.92 | 1 | 0.05 |
| Polyimide (Kapton) | 1.42 | 1 | 0.025 |
| Polypropylene (PP) | 0.9 | 1 | 0.01 |
| Polytetrafluoroethylene (PTFE) | 2.2 | 1 | 0.01 |

*Sample provided by DuPont.

The particular polymers were chosen to represent a wide range of solubilities to $^{129}$Xe and $^3$He gases. Each polymer sample was cleaned with ethanol and cut to a specific size and shape to provide a known volume and surface area of the polymer sample (normally V=2 cm$^3$, SA=42.6 cm$^2$) for each $T_1$ study.

The following steps were taken for each material measurement:

1. Clean the testing chamber
2. Polarize $^{129}$Xe or $^3$He
3. Perform a $T_1$ study to establish the chamber baseline ($T_{1c}$)
4. Place polymer sample in chamber
5. Polarize $^{129}$Xe or $^3$He
6. Perform a $T_1$ study of the chamber containing polymer same ($T_{1s}$)
7. Use $T_{1c}$ and $T_{1s}$ to find relaxation rate due to specific polymer The Polymer Sorption Model The ability to measure and calculate relaxivity can result in an understanding of the physical characteristics that differentiate materials. An initial study of a wide range of materials confirmed conventional rigid containers of glass are much better than containers of materials containing paramagnetic or ferrous constituents such as stainless steel. Notably, this test also showed a wide range of relaxivities within different material groups. In particular, different polymer materials were observed across the relaxivity spectrum. Manufacturing concerns such as durability and reliability make polymer materials an excellent alternative to the glass storage containers that are typically used for hyperpolarized gases. Scientifically, substantially pure samples of these materials allow for relatively less complex models of surface relaxation.

For discussion purposes, assume there is a polymer container of hyperpolarized gas in a homogeneous magnetic field. Since polymers are permeable materials, some quantity of gas dissolves in the container walls. The only dominant relaxation mechanism in this system is that of the hyperpolarized gas atoms interacting with the protons or contaminants in the surface and bulk of the polymer container. Driehuys et al. demonstrated that relaxation of hyperpolarized $^{129}$Xe in a specially coated glass sphere was dominated by the dipolar coupling between the protons in the surface and the $^{129}$Xe nuclear spin. See Driehuys et al., High-volume production of laser-polarized $^{129}$Xe, 69 App. Phys. Lett. (12), p. 1668 (1996). Since Xe—Xe collisions have a 56 hour $T_1$ and typical conventional material $T_1$ times are 2 hours or less, the relaxation rate of the free gas can be neglected. Gas dissolved in the polymer surface relaxes quickly (<1 second), so most of the hyperpolarized gas in the container is in the free gas form. Therefore, relaxation of this gas occurs through continual exchange between the free gas and the gas dissolved in the polymer. In material quantities, the rate of this gas exchange can be described by the "sorption parameters"—solubility ("S"), diffusion coefficient ("D"), and permeability ("P"). Permeability is the transmission of atoms or molecules through a polymer film. It depends on chemical and physical structure of the material as well the structure and physical characteristics of the permeant molecules. Permeability can be defined as the product of solubility and the diffusion coefficient. ("P=S×D"). Solubility ("S") is a measure of how much permeant can be dissolved in a given material. Diffusion coefficient ("D") is a measure of the random mobility of the atoms in the polymer. The polymer sorption parameters can be used to characterize the relaxation of hyperpolarized gases in the presence of permeable surfaces.

Relaxation in the Presence of Polymer Surfaces

Magnetization ("M") is defined as the product of the gas polarization "P" and the gas number density "[G]", M=[G]P. The equation governing relaxation of magnetization in the presence of a surface diffusion $$\frac{\partial}{\partial t}M(x,t) = D\frac{\partial^2}{\partial x^2}M(x,t) - \Gamma M(x,t) \quad (2.12)$$

where ("M(x,t)") is magnetization, ("D") is the diffusion coefficient of the gas in the surface material, and ("$\Gamma$") is the relaxation rate of the gas. See W. Happer et al., Hyp. Int. 38, pp. 435–470 (1987). As is customary, the solution is written as a product of spatial and time dependent components:

$$M(x,t) = m(x)e^{-t/T_1} \quad (2.13)$$

where ("m(x)") is the spatial distribution of magnetization on the surface. Substituting (2.15) into (2.13) yields the spatial equation:

$$\frac{\partial^2}{\partial x^2}m(x) = \frac{1}{D}\left(\Gamma - \frac{1}{T_1}\right)m(x) \quad (2.14)$$

Figure 2:
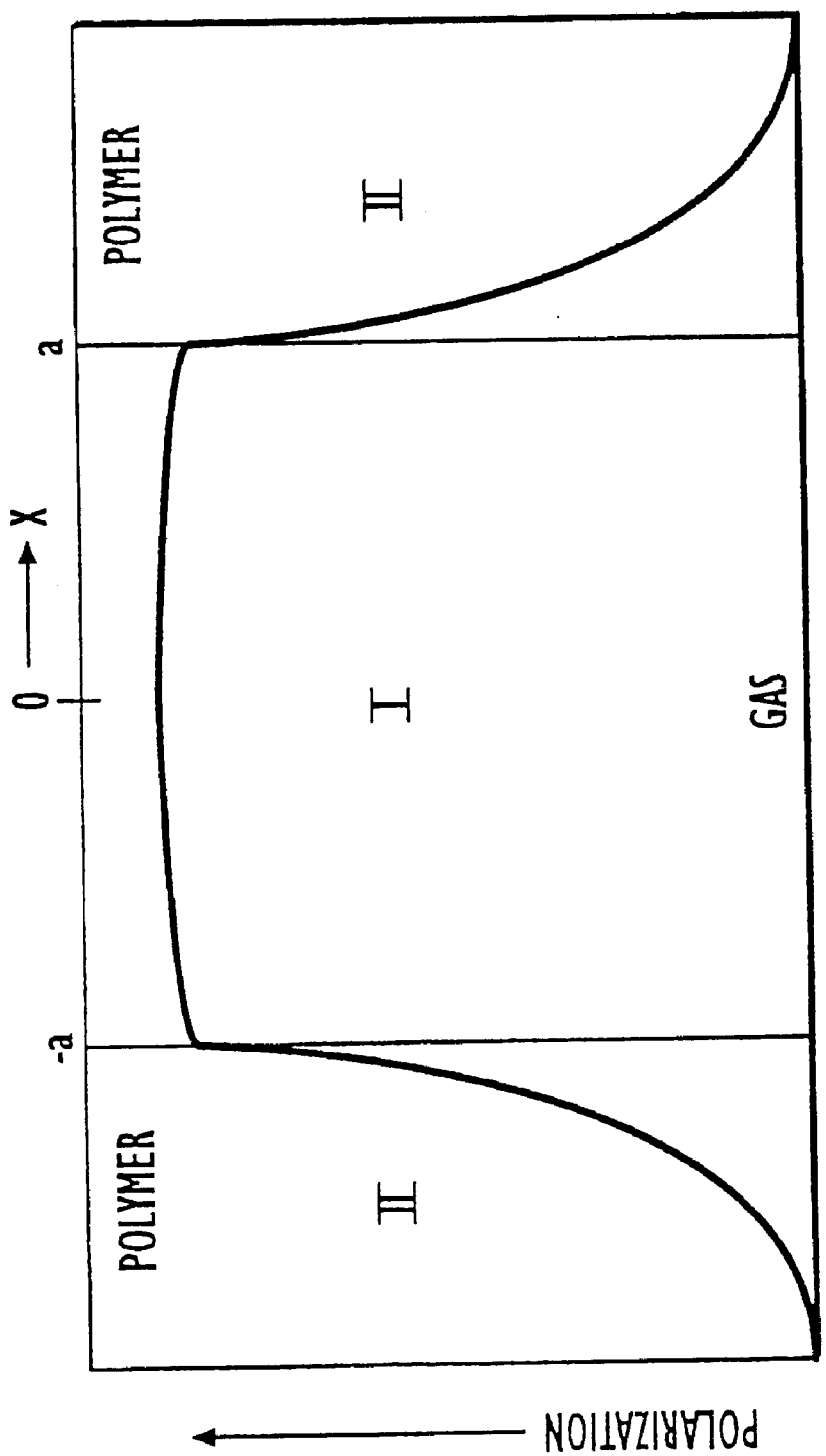
FIG. 2 is a graph showing the polarization level of a gas associated with the distance x the gas moves into a polymer.

This differential equation describes the spatial distribution of magnetization in the presence of diffusion and relaxation. Considering a one dimensional chamber shown in FIG. 2.

The chamber is a gas volume of width "2a" bounded on each side by infinite polymer walls. The polarization of gas in this chamber has two specific regions of interest. In the free gas portion of the container, the polarization is relatively homogenous with respect to spatial variable x. In contrast, polarization drops exponentially with distance x into the polymer surface. This profile reflects a much faster relaxation rate inside the polymer as opposed to in free space.

Equation (2.14) can be used to solve for the spatial magnetization of the gas and polymer regions independently. For a gas phase with diffusion coefficient $D_g$ and intrinsic relaxation rate $\Gamma_g=0$. Equation (2.14) becomes:

$$\frac{\partial^2}{\partial x^2}m_g(x) = -\frac{1}{D_g T_1}m_g(x) \quad \text{(RegionI)} \quad (2.15)$$

The first order symmetric solution to this equation is:

$$m_g(x) = A\cos(k_g x) \quad k_g^2 = \frac{1}{T_1 D_g} \quad \text{(RegionI)}$$

Similarly, the polymer region has diffusion coefficient "$D_p$" and relaxation rate $\Gamma_p$:

$$\frac{\partial^2}{\partial x^2}m_p(x) = \frac{1}{D_p}\left(\Gamma_p - \frac{1}{T_1}\right)m_p(x) \quad \text{(RegionII)} \quad (2.16)$$

One simplifying assumption is that the relaxation rate in the polymer is much faster than the observed relaxation rate ($\Gamma_p \gg 1/T_1$). Thus neglecting $1/T_1$ term in (2.16) yields a solution of the form:

$$m_p(x) = Be^{-k_p(x-a)} \quad k_p^2 = \frac{\Gamma_p}{D_p} \quad \text{(RegionII)}$$

These two solutions in conjunction with the appropriate boundary conditions can be used to solve for the observed $T_1$ of the gas in the polymer chamber. The first boundary condition ("BC") maintains continuity of polarization across the polymer gas boundary. Recalling that magnetization is the product of polarization and gas number density yields:

$$BC_1 : Sm_g(a) = m_p(a)$$

where ("S") is defined as the ratio of gas number densities, or the Ostwald Solubility "$S=N_p/N_g$". The secondary boundary condition ("BC2") arises because the exchange of magnetization across the gas-polymer boundary is equal on both sides. This exchange, known as the magnetization current, is defined as $J_m=-D\nabla m(x)$, yielding the boundary condition:

$$BC2 : D_g \frac{d}{dx}m_g(a) = D_p \frac{d}{dx}m_p(a)$$

Applying the boundary conditions to the solutions for magnetization in each of the two regions yields the following transcendental equation:

$$\tan k_g a = \frac{D_p k_p}{D_g k_g}S \quad (2.17)$$

This equation can be solved numerically, although a reasonable approximation is that $k_g a \ll 1$, so that tan $k_g a \approx k_g a$. In physical terms, this implies that the magnetization is spatially uniform across the gas phase. It also considers only the slowest of multiple diffusion modes. In order for this assumption to be false, the relaxation rate at the walls would have to be fast compared to the time it takes for the gas to diffuse across the chamber. Diffusion times are typically a few seconds, while common $T_1$ values are several minutes. Applying this assumption yields:

$$k_g^2 = S\frac{D_p k_p}{D_g a} \quad (2.18)$$

Substituting in $k_g$ and $k_p$ from the solutions to (2.15) and (2.16) gives:

$$\frac{1}{T_1} = \frac{S}{a}\sqrt{\Gamma_p D_p} \quad (2.19)$$

The relaxation rate in the polymer terms can be rewritten in terms of $\Gamma_p = 1/T_{1p}$. Solving for the relaxation time $T_1$:

$$T_1 = \frac{a}{S}\sqrt{\frac{T_1^p}{D_p}} \quad (2.20)$$

This analysis can be extended into three dimensions, yielding:

$$T_1 = \frac{V_c}{A_p S}\sqrt{\frac{T_1^p}{D_p}} \quad (2.21)$$

where $V_c$ is the internal volume of the chamber, A is the exposed surface area of the polymer and S is the solubility of the gas in the polymer.

The inverse relationship between $T_1$ and S is a key observation from this development. Because He solubilities are typically many orders of magnitude lower than corresponding Xe solubilities, $T_1$ times for $^3$He should be significantly longer than for $^{129}$Xe. There is also an apparent inverse square root dependence on the diffusion coefficient $D_p$. However, the relaxation time in the polymer $1/T_p$ also depends on $D_p$, canceling the overall effect on $T_1$. This leaves solubility as the dominant sorption characteristic in determining $T_1$.

Despite canceling out of (2.21) the diffusion coefficient plays a significant role in another quantity of interest, the length scale of the gas and polymer interaction. The exponential decay length scale of the polarization $L_p = 1/k_p$ is given by the solution to (2.16):

$$L_p = \sqrt{D_p T_1^p} \quad (2.22)$$

Importantly, this scale describes the depth into the polymer that the gas travels in the relaxation time period. In order to compare theoretical predictions to experimental data, it is preferred that material samples be at least several length scales thick. This ensures that the surface model developed here which assumes infinite polymer thickness is an accurate approximation of the diffusion process. For reference, LDPE has a diffusion constant of 6.90e-6 cm$^2$/s for He gas and hyperpolarized $^3$He has a relaxation time in the polymer of about 0.601 s ($T_1^P = 0.601$ seconds). The resulting length scale is about 20 $\mu$m, many times smaller than the 1 mm polymer samples used in the study described herein.

Predicting $T_1$ Values Using Sorption Model

Using equation (2.21) to predict $T_1$ values for hyperpolarized gases in the presence of various polymer surfaces requires knowledge of the test environment ($V_c$, $A_p$), as well as parameters linking the specific gas and polymer ($T_1^P$, S and D). Unfortunately, the solubility and diffusion data linking gas and polymers is scattered and sometimes nonexistent. On the other hand, the test environment is typically known. Advantageously, this data can be used to calculate the $T_1^P$.

As discussed earlier, the relaxation mechanism that dominates hyperpolarized gas relaxation in polymers is the interaction with the nuclear magnetic moments of the hydrogen nuclei (in hydrogen based polymers). Generally stated, in the absence of paramagnetic contaminants, the $^1$H nuclei are the only source of magnetic dipoles to cause relaxation. Based on this interaction, Huang and Freed developed an expression for the relaxation rate of spin ½ gas diffusing through a polymer matrix. See L. P. Hwang et al., Dynamic effects of pair correlation functions on spin relaxation by translational diffusion in liquids, 63 J. Chem. Phys. No. 9, pp. 4017–4025 (1975); J. H. Freed, Dynamic effects of pair correlation functions on spin relaxation by translational diffusion in liquids. II. Finite jumps and independent $T_1$ processes, 68 J. Chem. Phys. Vol. 9, pp. 4034–4037 (1978); and E. J. Cain et al., Nuclear Spin Relation Mechanisms and Mobility of Gases in Polymers, 94 J. Phys. Chem. No. 5, pp. 2128–2135 (1990). This results in the following expression in a low magnetic field B regime (B<1000 Gauss).

$$T_1^p = \frac{405}{32\pi}\frac{D_p^b}{s(s+1)\gamma_G^2\gamma_H^2 h^2 N_a[^1H]} \quad (2.23)$$

In this formula, $\gamma_g$ is the gyromagnetic ratio of the noble gas, $\gamma_H$ is the gyromagnetic ratio of the protons, s is the proton spin number (½). $N_a$ is Avogadro's number, [$^1$H] is the molar density of protons in the matrix, and b is the distance of closest approach of the noble gas to a proton. The dipole interaction equations have an inverse square dependence on the gyromagnetic ratios $\gamma_g$ and $\gamma_h$. As noted before, substituting this form into Equation (2.21) cancels $D_p$ from the relaxation expression. This leaves only solubility (S) to effect the $T_1$ in various polymers. The other significant factor in (2.23) is the [$^1$H]$^{-1}$ dependence. As such, since protons in the polymer are the dominant relaxation mechanism, high concentrations will adversely affect $T_1^P$.

Implementing this expression for $T_1^P$ requires the appropriate physical parameters in CGS units. Table 2.1 shows an example of the approximate values used for this calculation performed for relaxation of $^{129}$Xe in low-density polyethylene (LDPE):

TABLE 2.1

Sample Data for $T_1^P$ of $^{129}$Xe in LDPE

| | |
|---|---|
| $\gamma_g$ (G$^{-1}$s$^{-1}$) = | 7.40e03 |
| $\gamma_h$ (G$^{-1}$s$^{-1}$) = | 2.68e04 |
| h (erg s) = | 6.63e-27 |
| [$^1$H] (mol/L) = | 131.43 |
| b (cm) = | 2.40e-08 |
| $D_g$ (cm$^2$s$^{-1}$) = | 6.90e-08 |
| $T_1^P$ (s) = | 0.0653 |

*One of few available literature values (Polymer Handbook)

Confirmation of Predictive Model

The development of the sorption based relaxation model along with the experimental apparatus to test relaxivity allows the comparison of a theoretical model of surface relaxation with experimental results. Confirmation of this model enables quantitative predictions of surface relaxation for selecting appropriate and preferred materials to contact hyperpolarized gases. The spin down station was used to measure the relaxation effects of 7 different polymers on hyperpolarized $^{129}$Xe and $^3$He. In order to compare this experimental data with the theoretical, solubility of both gases in each polymer was measured. These sorption measurements are described below as well as a discussion of results from the $^{129}$Xe and $^3$He polymer studies.

Solubility Measurements

Solubility ("S") is the only remaining unknown in the formula to predict $T_1$ of hyperpolarized gases in polymers (2.21) the equation is related here for reference:

$$T_1 = \frac{V_c}{A_p S} \sqrt{\frac{T_1^p}{D_p}}$$

Sorption data for various polymers is tabulated in sources such as the Polymer Handbook. S. Pauly, Permeability and Diffusion Data, The Polymer Handbook VI/435. Unfortunately, while data for He is widely available (although prone to error), there has not been a need to measure sorption characteristics of Xe in different polymers. The lack of published Xe solubilities resulted in a search for equipment to measure these quantities. The polymer group at the Chemical Engineering Department at North Carolina State University measured the solubility of both Xe and He gases in the 7 polymers that were to be used to verify the polymer relaxation theory. The results of He and Xe solubility measurements are compared to the available literature values in Table 4.1 below.

TABLE 4.1

Results of Solubility Measurements

|  | S (Xe) (lit.) | S (Xe) (meas.) | S (He) (lit.) | S (He) (meas.) |
|---|---|---|---|---|
| LDPE | 0.59 | 0.68± | 0.0055 | 0.006± |
| HDPE | — | 0.42± | 0.0028 | 0.004± |
| PP | — | 0.70± | 0.0002 | 0.020± |
| PTFE | 0.75 | 0.70± | 0.1104 | 0.003± |
| Nylon 6 | — | .31 | 0.0043* | .003 |
| Silicone | 3.99 | 1.93± | 0.0430 | 0.034± |
| PI | — | 4.00 ± 0.1 | 0.0056 | 0.030± |

*Literature value for Nylon 11.

The measurements were obtained by placing polymer samples in an evacuated chamber. A known pressure of gas was then introduced into the chamber. As the gas dissolved into the polymer, the decrease in chamber pressure was recorded. By knowing the volume of the test chamber and carefully maintaining the temperature of the apparatus, the solubility of the gas in the polymer can be calculated from the pressure vs. time data. However, there are many intrinsic difficulties in polymer sorption measurements. Because of the low diffusion coefficients in some polymers such as polyimide, it can take a long time for gas to permeate the entire sample and establish equilibrium. Even the thinnest samples available must be allowed to remain in the chamber for many days. Another problem, evident in He measurements, is that pressure differences observed for materials with low solubilities are extremely small, resulting in significant measurement uncertainty. In addition these to problems, density values play an important role in the solubility calculation. While the manufacturer provides density estimates for the material samples, laboratory measurements confirmed that these values were often inaccurate. This discrepancy can be responsible for dramatic changes in the final solubility value. It should therefore be noted that relative to the sorption measurements, more reliable results could be obtained. However, the values provided are sufficient to confirm the solubility based relaxation theory.

$^{129}$Xe Materials Study

The majority of this materials study was performed using hyperpolarized $^{129}$Xe. A much greater sensitivity of $^{129}$Xe to surface effects resulted in shorter $T_1$ times and allowed for more rapid testing of materials. More dramatic relaxation effects eliminate the need for an extremely long chamber $T_1$ as is the case for $^3$He studies. This fact alone resulted in more reliable results for $^{129}$Xe materials testing.

Figure 3:
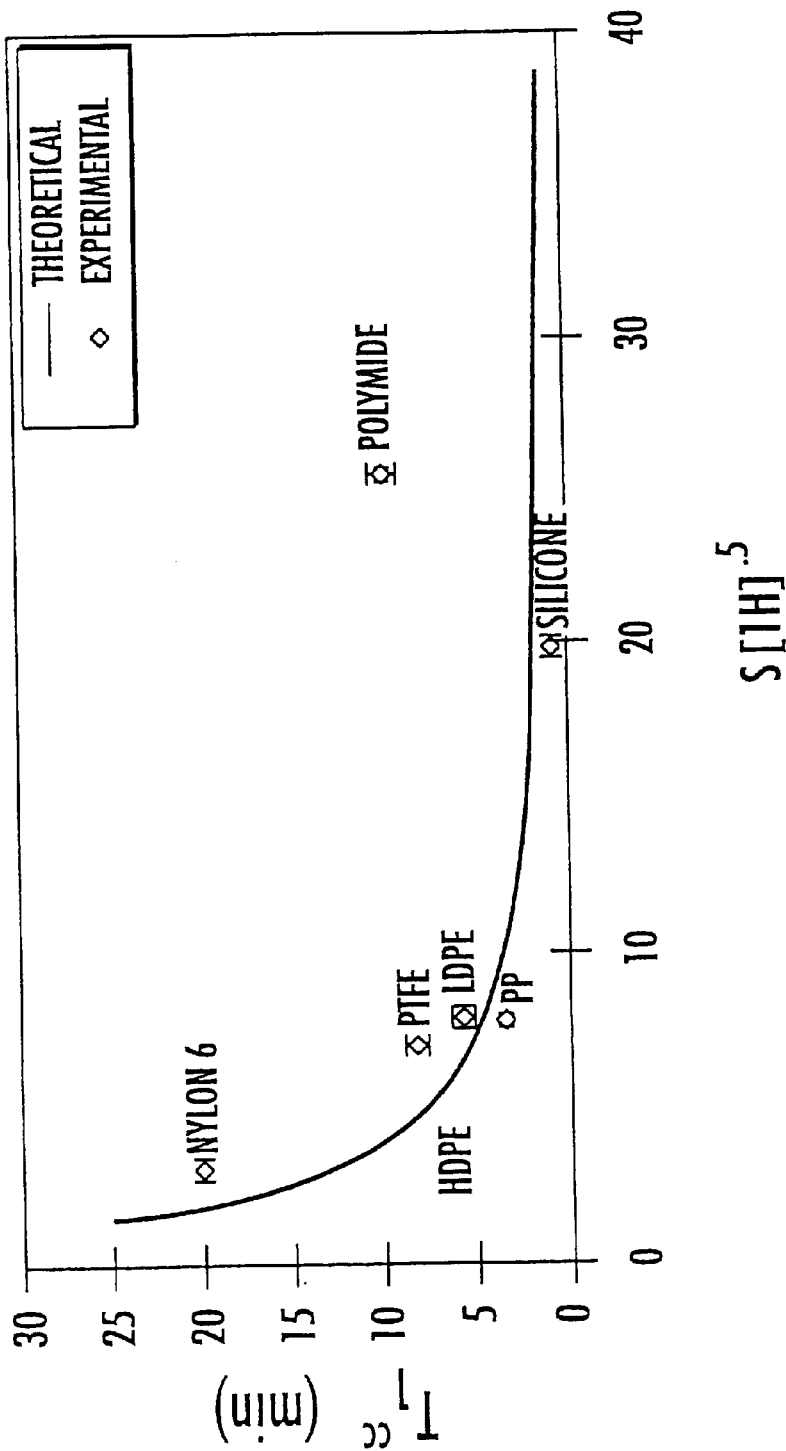
FIG. 3 is a graph showing the results of the standardized relaxation times plotted against solubility (measured and theoretical) for various materials ($T_1^{cc}$ representing the relaxation time for $^{129}$Xe hyperpolarized gas in a one cubic centimeter sphere).

FIG. 3 is a plot of $T_1^{cc}$ vs. the product $S[1H]^{-5}$, representing the two significant terms in the expression for $T_1$ (2.21) developed in the polymer sorption relaxation model. For the experimental data points, the y error bars on the graph represent the cumulative error in the relaxation measurement. The x error bars are associated with the solubility measurements described above. The data confirms that solubility can be used to predict $T_1$ for hyperpolarized $^{129}$Xe on polymer surfaces. While the experimental data points follow the trend predicted by the theoretical model remarkably well, certain discrepancies merit further discussion.

Lower than predicted $T_1$ measurements as in the case of silicone can be explained in several ways. Paramagnetic impurities in the material sample or test chamber are the primary suspect. Recall that only protons were assumed to have a depolarizing effect on the hyperpolarized gas. In order for this assumption to hold true, the composition of the material sample would have to be extremely pure. For example, given that the gyromagnetic ratios of Fe and protons are related $Y_{Fe} \sim 1000 Y_{1H}$, a one part per thousand presence of Fe in the material sample can double the relaxation rate. Although the sample surfaces were cleaned with high-purity ethanol prior to testing in the Spin Down Station, paramagnetic impurities can be trapped in the polymer matrix during the curing process. One possible contaminant is Pt metal (which is paramagnetic) that can be used in the mold forming silicone polymers.

When considering factors that cause the measured $T_1$ results to be higher than predicted as in the case of polyimide (PI) and PTFE, the diffusion coefficient becomes an important parameter. For polyimide, the diffusion of Xe into the polymer is so slow that it takes weeks for the Xe to equilibrate completely. This time scale is much longer than the 1–2 hour time scale of the relaxation measurements. Since the $T_1^p$ of $^{129}$Xe in PI is on the order of 100 ms (based on LDPE), the $^{129}$Xe atoms only sample a tiny layer (~5 μm, based on a diffusion coefficient D~$10^{-8}$ cm$^2$/s), of the surface of the polymer sample. This surface layer may have different sorption characteristics than the bulk polymer that was used in the solubility measurements. While solubility can typically only be measured for the bulk sample, the region of interest is only 0.5 μm out of 1 mm, or ¹⁄₁₀₀₀ of the actual sample.

A summary comparison of the predicted and measured results for $^{129}$Xe is presented in Table 4.2. More detailed results from the theoretical and experimental calculations are tabulated in FIG. 5.

TABLE 4.2

Results of Polymer Relaxation Study for $^{129}$Xe

|  | S | Pred. Y (cm/min) | Pred. $T_1^{cc}$ (min) | Measured Y (cm/min) | Measured $T_1^{cc}$ (min) |
|---|---|---|---|---|---|
| LDPE | 0.68 | 0.0419 | 4.94 | 0.0370 ± 0.0039 | 5.59 ± 0.59 |
| HDPE | 0.42 | 0.0263 | 7.87 | 0.0362 ± 0.0025 | 5.71 ± 0.39 |
| PP | 0.70 | 0.0427 | 4.85 | 0.0540 ± 0.0035 | 3.83 ± 0.25 |
| PTFE | 0.75 | 0.0356 | 5.82 | 0.0249 ± 0.0016 | 8.30 ± 0.54 |
| Nylon 6 | .31 | .0166 | 12.5 | 0.0104 ± 0.0016 | 19.91 ± 2.99 |
| Silicone | 1.93 | 0.1066 | 1.94 | 0.3112 ± 0.0072 | 0.67 ± 0.02 |
| PI | 4.10 | 0.1345 | 1.54 | 0.0212 ± 0.0017 | 9.78 ± 0.78 |

³He Material Studies

The study of ³He surface relaxation on polymers is much more challenging than the study of $^{129}$Xe. FIG. 4 shows the results of this study in the $T_1^P$ vs. $S[1H]^{-5}$ form as discussed for the $^{129}$Xe presented in FIG. 3. The various errors associated with the ³He study make direct comparison with the $^{129}$Xe difficult. However, there are trends linking the two studies worth noting.

The results for LDPE and PTFE agree extremely well with theory. However, the other materials in the ³He study fall short of predicted $T_1$ relaxation times. Of these materials, silicone, PP and HDPE are consistent with short results observed in the $^{129}$Xe study.

This trend points to paramagnetic impurities in the material samples. These contaminants can include dust, fingerprints, Apiezon grease, and ferrous impurities that may be trapped in the polymer material. Unfortunately, higher diffusion coefficients for lie result in much longer length scales (~20 μm ³He vs.~1 μm $^{129}$Xe, Equation 2.23) for polymer gas interaction. The greater mobility of gas atoms in the polymer results in much deeper sampling of the polymer. This sampling could significantly increase the probability of interaction with paramagnetic impurities if their distribution in the polymer is non-uniform. For example, gas in silicone has a large diffusion coefficient (DHe~4e-5, DXe~5e-6) relative to other polymers in the study. While the measured $T_1$ for silicone, PP, and HDPE was lower than predicted in both $^{129}$Xe and ³He studies, the ³He has a length scale roughly 3 times that of $^{129}$Xe. This contaminant concern magnifies the importance of sample preparation in the study of surface effects as well as the preparation of containers used for hyperpolarized gases. As discussed with the $^{129}$Xe study, sample preparation included only a surface cleaning, leaving any contaminants contained within the polymer matrix. One alternative can be to use acid baths to clean containers or container materials to remove or minimize at least surface and proximate sub-surface impurities potentially embedded in the polymer matrix.

Of the remaining polymers in the ³He study, only polyimide (PI) and nylon 6 show markedly different results between the two studies. One distinction that might explain this result is the difference between amorphous and semicrystalline polymers. LDPE, HDPE, and PP are amorphous polymers that should exhibit uniform solubility. Alternatively, semicrystalline polymers such as PTFE, nylon 6, and PI might exhibit spatial diffusion and thus exhibit regional solubilities that differ from the bulk solubility measured in the polymer lab.

A summary comparison of the predicted and measured results for ³He is presented in Table 4.3. (Detailed results in FIG. 5).

TABLE 4.3

Results of Polymer Relaxation Study for ³He

|  | S | Pred. Y (cm/min) | Pred. $T_1^{cc}$ (min) | Measured Y (cm/min) | Measured $T_1^{cc}$ (min) |
| --- | --- | --- | --- | --- | --- |
| LDPE | 0.0060 | 0.0012 | 170.98 | 0.0012 ± 0.00015 | 170.80 ± 21.22 |
| HDPE | 0.0040 | 0.0008 | 252.40 | 0.0056 ± 0.00055 | 36.65 ± 3.66 |
| PP | 0.0067 | 0.0013 | 154.81 | 0.0211 ± 0.00156 | 9.80 ± 0.77 |
| PTFE | 0.1104 | 0.0158 | 13.09 | 0.0150 ± 0.00071 | 13.72 ± 0.65 |
| Nylon 6 | .003 | .0005 | 395 | 0.0026 ± 0.00034 | 79.98 ± 11.17 |
| Silicone | 0.0340 | 0.0061 | 33.69 | 0.0386 ± 0.00169 | 5.36 ± 0.22 |
| PI | 0.0300 | 0.0032 | 64.30 | 0.0055 ± 0.00054 | 37.58 ± 3.78 |

$O_2$ Contamination

Impurities introduced into the test environment could also account for measurement errors. Dust, fingerprints, and other contaminants may be introduced into the test chamber when the chamber is opened to insert the sample. All of these contaminants have a depolarizing effect that is not included in the sorption model. The most significant confirmed contaminant in the test environment is the presence of $O_2$ in the test chamber.

Because $O_2$ has a magnetic moment, it can relax hyperpolarized gases in the same manner as protons. While $O_2$ affects $^{129}$Xe and ³He similarly, the longer $T_1$ times associated with the ³He study magnify any $O_2$ contamination. For example, 1 Torr of $O_2$ in the chamber would generally not be noticed on the time scale of the $^{129}$Xe study but would have a radical impact on ³He studies. The effect of $O_2$ in the test chamber was observed on several occasions. It resulted in a non exponential decay rate many times faster than the predicted $T_1$ of the sample.

While in storage, oxygen from the atmosphere diffuses and sorbs into the polymer sample. In order to remove this $O_2$ from the polymer, the sample is preferably left under vacuum for a period of time before testing. The time period necessary for this degassing to take place can be calculated if diffusion coefficients are available. Table 4.5 shows the degassing calculations for 1 mm thick polymer samples with available $O_2$ diffusion coefficients, assuming $t \approx (Z)^2/D$ (Z=sample thickness).

TABLE 4.5

$O_2$ Degassing Time for ³He Relaxation Studies

| Material | D($O_2$) cm²/s | Volume $O_2$ in Polymer cc (STP) | Vacuum Time Hr |
| --- | --- | --- | --- |
| LDPE | 6.80e-06 | 0.0201 | 0.41 |
| HDPE | 3.07e-06 | 0.0077 | 0.90 |
| PP | 1.95e-05 | * | 0.14 |
| PTFE | 8.11e-07 | 0.0893 | 3.43 |
| Silicone | 4.10e-05 | 0.1302 | 0.07 |

*no S($O_2$) available for PP

In determining the relaxation time ($T_1$) of a hyperpolarized noble gas in a polymer container equation 2.21, can be restated as:

$$T_1 = \frac{V}{AS}\sqrt{\frac{T_1^p}{D_p}} \quad (2.21)$$

where "V" is the container volume, "A" is the container surface area, "S" is the Ostwald solubility of the noble gas in the polymer, "$T_1^P$" is the relaxation time of the noble gas dissolved in the polymer matrix, and "$D_p$" is the diffusion coefficient of the noble gas in the polymer. This quantitative analysis reveals that the relaxation time of the noble gas is inversely proportional to noble gas solubility in the polymer. Indeed, and surprisingly, as noted above, the surface induced relaxation time is believed to be proportional to the square root of the noble gas relaxation time in the polymer matrix.

Restating the multiple constants of equation 2.23 into a factor "C" results in:

$$C = \frac{32\pi h^2 Na}{4.05 \times 10^5} \quad (2.23a)$$

Thus, the relaxation rate of a noble gas in the polymer can be expressed as stated in equation (2.23b (I=proton spin)).

$$\frac{1}{T_1^p} = \frac{C\gamma_G^2\gamma_H^2 I(I+1)}{bD_p}[^1H] \qquad (2.23b)$$

Inserting this relaxation rate expression into equation (2.21') shows that the dependence on diffusion coefficient disappears and results in a surface relaxation time "$T_1$" which can be expressed by equation (2.23c).

$$T_1 = \frac{V}{AS\gamma_G\gamma_H}\sqrt{\frac{b}{CI(I+1)[^1H]}} \qquad (2.23c)$$

This expression can be used to predict the relaxation time of hyperpolarized noble gases such as either $^3$He or $^{129}$Xe on any polymer surface. As was pointed out in U.S. Pat. No. 5,612,103, perdeuteration of the polymer should lead to improvement in the noble gas relation time. However, this improvement appears to be less than what was previously predicted. The gyromagnetic ratio $\gamma_D$ of deuterium is 6.5 times smaller than for hydrogen, and the spin "I" is 1. A comparison of the relaxation time of the noble gas in the perdeuterated polymer matrix versus its normal counterpart shows the following:

$$\frac{T_p(D)}{T_p(H)} = \frac{(1/2)(1/2+1)(26750)^2}{(1)(1+1)(4106)^2} = 15.9 \qquad (2.30)$$

However, this improvement in $T_p$ translates into an overall improvement in relaxation time of about 4 (the square root of 15.9). Thus, deuteration is still desired but perhaps is not as impressive as was previously expected.

A comparison of $^3$He relaxation with $^{129}$Xe relaxation on a given polymer surface can now be made using equation (2.23c) assuming that "b" does not vary substantially for the two gases as expressed in equation (2.31).

$$\frac{T_1(^3He)}{T_1(^{129}Xe)} = \frac{S_{Xe}\gamma_{Xe}}{S_{He}\gamma_{He}} \qquad (2.31)$$

For example, in low-density polyethylene ("LDPE"), the ratio of xenon solubility to helium solubility is 107 and the ratio of $\gamma_{Xe}/\gamma_{He}$=0.37. Thus, the relaxation time of $^3$He on a LDPE surface will be nearly 40 times longer than for $^{129}$Xe.

Further, as noted above, the noble gas polarization level is not spatially uniform in the polymer. The polarization is constant for the gaseous phase but falls off exponentially with distance into the polymer.

Therefore, it is important to note that especially in the case of polymer coatings, the thickness of the coating preferably exceeds the polarization decay length scale "$L_p$" (equation 2.22) in order for the gas depolarization time to depend on the polymer properties in a predictable way. For a coating thickness less than "$L_p$", polarized gas can sample the substrate underneath the polymer, and potentially undergo undesirably fast relaxation. Because "$T_p$" also depends linearly on "$D_p$," the depolarization length scale is proportional to the gas diffusion coefficient. Thus, especially for $^3$He, which tends to have a high diffusion constant, the polymer contact layer, or the thickness of the coating or film is preferably several times the critical length scale. Preferably, the thickness is above about 16 micrometers and more preferably at least 100–200 micrometers thick in order to be effective. In fact, coatings that are substantially thinner than "$L_p$" can be more deleterious than having no coating at all, because the mobility of the noble gas once into the coating is reduced. As such, a noble gas dissolved in a thin coating can interact with the surface underneath for a much longer period of time than if the coating were not present. Indeed, the probability of depolarization appears to increase as the square of the interaction time.

The relatively long relaxation times achievable with polymers (coatings or container materials) make the development of polymer bags for hyperpolarized gas storage appealing. Further, bags are an ideal storage and delivery device for magnetic resonance imaging using inhaled hyperpolarized $^3$He because the gas can be completely extracted by collapsing the bag. In contrast, a rigid container typically requires a more sophisticated gas extraction mechanism.

$O_2$ Induced Relaxation

When bags with long surface relaxation times are used, other relaxation mechanisms can become important. One of the most important additional relaxation mechanisms is due to collisions of the noble gas with paramagnetic oxygen as noted above. Saam et al. have shown that the relaxation time of $^3$He due to collisions with paramagnetic oxygen can be expressed as stated in equation (2.32).

$$T_1[O_2]=2.27 \text{ s amgt} \qquad (2.32)$$

(Note amagat is abbreviated as "amgt") (1 amagat= $2.689\times10^{19}$ atoms/cm$^3$, the density of an ideal gas at 273 K and 1 atm.). See B. Saam, W. Happer and H. Middleton, Nuclear relaxation of $^3$He in the presence of $O_2$, Phys. Rev. A, 52, 862 (1995). Thus, a pressure of oxygen as small as $^1/_{1000}$ of an atmosphere can result in a $^3$He relaxation time of only 38 minutes even with perfect surfaces. Given this problem, tremendous care should be taken to reduce the oxygen content in the storage container through careful preconditioning of the container, such as by pumping and pure gas purging methods. However, even with preconditioning, a bag is susceptible to permeation of oxygen through the polymer which can disadvantageously build substantial oxygen concentration over time. The volume of oxygen transmitted through the polymer material depends on several factors, including the polymer-specific oxygen permeability coefficient "$Q_{O2}$". For small quantities of oxygen transfer, the rate of oxygen concentration build-up in the bag is nearly constant, and can be expressed by equation (2.33).

$$\frac{d}{dt}[O_2] = \frac{A\Delta P_{O2}}{V_{bag}\Delta x}Q_{O2} \qquad (2.33)$$

"[$O_2$]" is the oxygen concentration in the bag, "A" is the polymer surface area, "$\Delta P_{O2}$" is the oxygen pressure difference across the bag surface, "$V_{bag}$" is the volume of the bag, "$\Delta x$" is the polymer thickness, and "$Q_{O2}$" is the oxygen permeability coefficient. Using equation (2.33) and a bag having the following characteristics (area=648 cm$^2$, volume=1000 cm$^3$, $\Delta\chi$=0.01$\chi$ cm, P=0.2×10$^5$Pa, $Q_{O2}$ (LDPE)=2.2×10$^{-13}$ cm$^2$/S Pa) gives a d/dt($O_2$) value of about 2.8×10$^{-7}$ amgt/s. Thus, a one hour duration (3600 seconds) will give a 1×10$^{-13}$ amgt, which corresponds to a $T_1$ of about 38 minutes. For Tedlar™, the $O_2$ permeability is smaller (0.139×10$^{-13}$–158 times less permeable than LDPE). Thus, in this material, one hour of permeation will give an $O_2$ induced $T_1$ of about 99 hours, but after 10 hours the $T_1$ drops to only 10 hours. Thus, as an alternative to an $O_2$ shield placed over the inner layer, the contact surface layer itself can be formed as a polymer having reduced permeability to $O_2$ and/or with increased thickness $\Delta x$.

Accordingly, oxygen-induced relaxation can quickly dominate surface relaxation even when careful gas handling techniques are employed. Therefore, in order to make polymer bags a viable storage medium, another layer of material is preferably used to suppress oxygen permeability. So long as the thickness of polymer in contact with the polarized gas is greater than $L_p$, the secondary material used for oxygen permeability suppression does not need to be non-depolarizing. A metal film such as aluminum can be very effective in such an application.

Materials

A comparison of the experimentally measured relaxation times to the theoretical values reveals remarkable agreement for the polymer systems for which $^{129}$Xe solubilities are known. Theoretical relaxation times are also calculated for $^3$He on a variety of polymer surfaces/systems. The results are summarized in FIGS. 5 and 6. The relaxation times have been scaled to a 1 cm$^3$ spherical container.

Note that the results for $^{129}$Xe in the fluoropolymer PTFE (Teflon™) are also shown in FIGS. 5 and 6. For this case, for a one cubic centimeter ("cm$^3$") spherical container, the calculated $T_1$ was 5.65 min and the observed relaxation time was 8.3 min. The calculations are identical to those discussed previously except for the substitutions in the equations and a subtle change in "b" due the larger size of the fluorine atom compared to the hydrogen atom. The composition of the atomic structure of the material is different (i.e., fluorine not hydrogen atom). In fact, with the possible exception of Tedlar™ (polyvinylfluoride), most fluoropolymers are not particularly good for the preservation of either $^{129}$Xe or $^3$He hyperpolarization. For example, the predicted $T_1$ for $^3$He on PTFE is only 13.1 minutes in a 1 cm$^3$ sphere. This is due to a relatively high solubility of helium in most fluropolymers due to that larger void space in the polymer resulting from the large fluorine atoms. Furthermore, most common gasket materials such as Viton™, Kel-F™, and Kalrez™, are fluropolymers and can potentially be substantially depolarizing to $^3$He compared to pure hydrocarbon gaskets such as those containing polyolefins. Examples of preferred seal materials include polyolefins such as polyethylene, polypropylene, and copolymers and blends thereof.

Because the shape of the container area can impact the rate of depolarization, it is preferred that container configurations be selected to maximize the free-gas volume of the container (V) while minimizing the surface area (A) which contacts the hyperpolarized gas (that is, to decrease the value of the ratio A/V). More preferably, the container is sized and configured to provide a A/V ratio of about less than 1.0, and even more preferably less than about 0.75. In one embodiment, the container is substantially spherical, such as a round balloon-like container.

Preferred polymers for use in the inventions described herein include materials which have a reduced solubility for the hyperpolarized gas. For the purposes of the inventions herein, the term "polymer" to be broadly construed to include homopolymers, copolymers, terpolymers and the like. Similarly, the terms "blends and mixtures thereof" include both immiscible and miscible blends and mixtures. Examples of suitable materials include, but are not limited to, polyolefins (e.g., polyethylenes, polypropylenes), polystyrenes, polymethacrylates, polyvinyls, polydienes, polyesters, polycarbonates, polyamides, polyimides, polynitriles, cellulose, and cellulose derivatives and blends and mixtures thereof. It is more preferred that the coating or surface of the container comprise a high-density polyethylene, polypropylene of about 50% crystallinity, polyvinylchloride, polyvinylflouride, polyamide, polyimide, or cellulose and blends and mixtures thereof.

Of course, the polymers can be modified. For example, using halogen as a substituent or putting the polymer in deuterated (or partially deuterated) form (replacement of hydrogen protons with deuterons) can reduce the relaxation rate. Methods of deuterating polymers are known in the art. For example, the deuteration of hydrocarbon polymers is described in U.S. Pat. Nos. 3,657,363, 3,966,781, and 4,914,160, the disclosures of which are hereby incorporated by reference herein. Typically, these methods use catalytic substitution of deuterons for protons. Preferred deuterated hydrocarbon polymers and copolymers include deuterated paraffins, polyolefins, and the like. Such polymers and copolymers and the like may also be cross-linked according to known methods.

It is further preferred that the polymer be substantially free of paramagnetic contaminants or impurities such as color centers, free electrons, colorants, other degrading fillers and the like. Any plasticizers or fillers used should be chosen to minimize any magnetic impurities contacting or positioned proximate to the hyperpolarized noble gas.

Alternately, the first layer or contact surface can be formed from a high purity (and preferably non-magnetic) metal. The high purity metal can provide advantageously low relaxivity/depolarization resistant surfaces relative to hyperpolarized noble gases. Preferred embodiments will be discussed further below. Of course, the high purity metal film can be combined with the materials discussed above or can be used with other materials to form one or more layers to provide a surface or absorption region which is resistant to contact depolarization interactions.

As noted above, any of these materials can be provided as a surface coating on an underlying substrate or formed as a material layer to define a friendly contact surface. If used as a coating, the coating can be applied by any number of techniques as will be appreciated by those of skill in the art (e.g., by solution coating, chemical vapor deposition, fusion bonding, powder sintering and the like). Hydrocarbon grease can also be used as a coating. As noted above, the storage vessel or container can be rigid or resilient. Rigid containers can be formed of Pyrex# glass, aluminum, plastic, PVC or the like. Resilient vessels are preferably formed as collapsible bags, preferably collapsible polymer or metal film bags.

Containers

Figure 7:
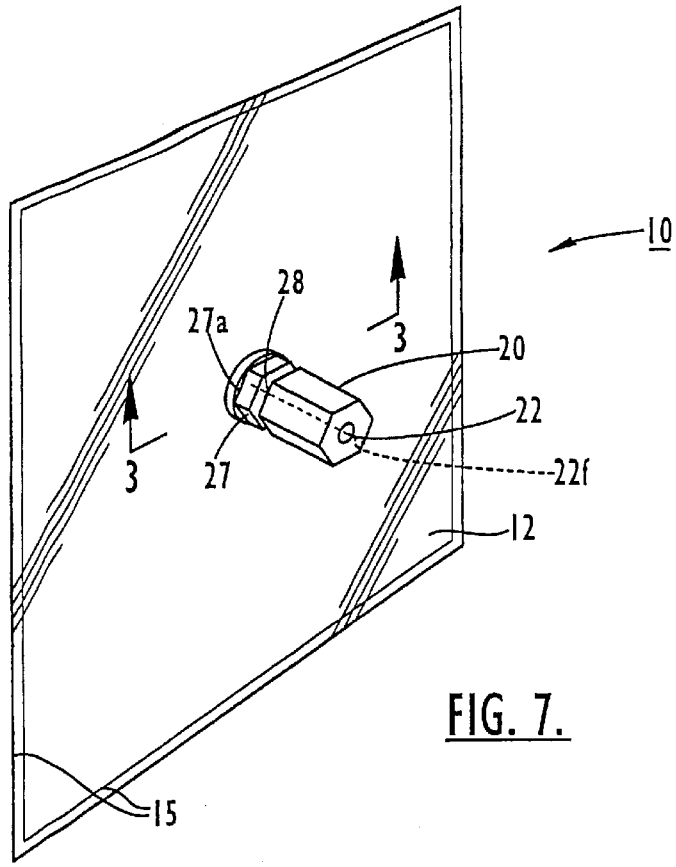
FIG. 7 is a perspective view of a hyperpolarized gas container according to one embodiment of the present invention in a deflated state.
Figure 8:
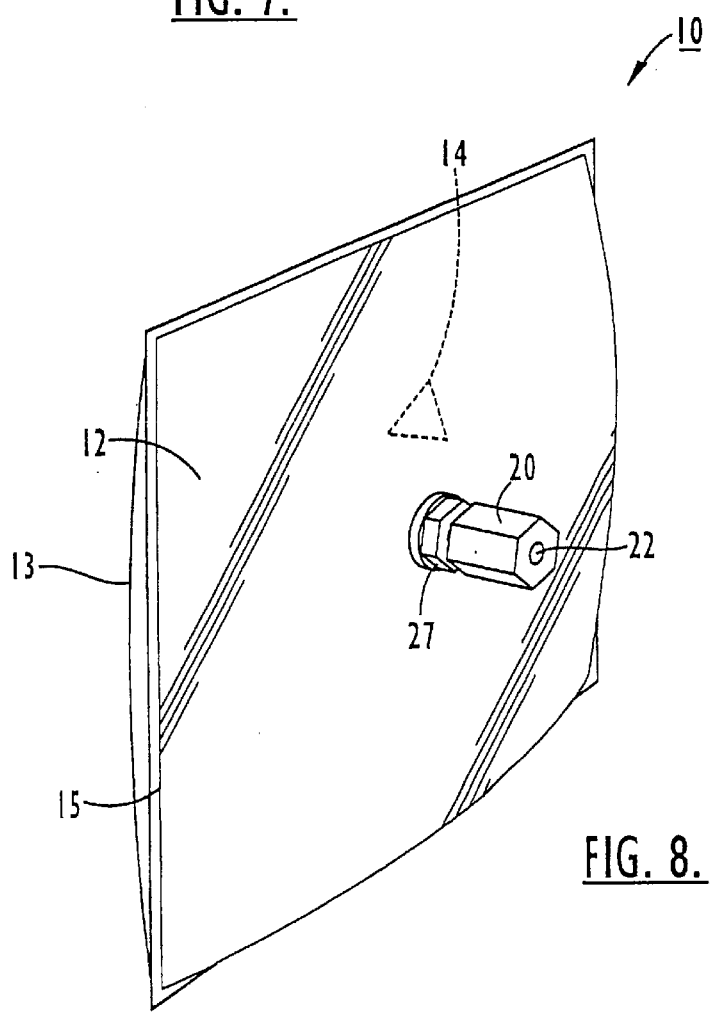
FIG. 8 is a perspective view of the container of FIG. 7, shown in an inflated state.

Turning now to the drawings, FIGS. 7 and 8 illustrate a preferred embodiment of a container 10 for hyperpolarized gas according to the instant invention. FIG. 7 shows the container 10 in the collapsed (empty) position and FIG. 8 shows the container 10 when inflated (filled). As shown, the container 10 includes a front wall 12 and a rear wall 13. The walls 12, 13 are joined by a perimeter seal 15. The front wall 12 also includes a coupling member 20 and an entry port 22. The coupling member is preferably configured to releasably attach to the hyperpolarizer apparatus and an end delivery device. Preferably, the coupling member 20 and perimeter seal 15 are configured to withstand about 0.5–3 atm of pressure, and more preferably about 0.8–1.25 atm of pressure. Preferably, as shown, the coupling member 20 is attached to the front wall via a seal 25 to facilitate the airtight arrangement of the interface between the wall 12 and the coupling member 20.

FIG. 9 illustrates a sectional view of the container 10. The front and rear walls 12, 13 define a chamber 30 which expands to receive a quantity of hyperpolarized gas therein. The entry port 22 is in fluid communication with the chamber 30. In operation, the hyperpolarized gas is directed through the entry port 22 into the chamber 30 thereby forcing the container 10 to expand (FIG. 8) and capture the hyperpolarized gas.

In a preferred embodiment, as shown in FIGS. 9 and 12, the walls 12, 13 are configured with two layers 41, 44. The first layer 41 includes the inner contact surface 12a of the chamber 30 that holds and thus contacts the hyperpolarized gas. As such, the hyperpolarized noble gas is susceptible to contact induced depolarization depending on the type of material and the depth of the material used to form this layer. Thus, this surface is preferably formed by a coating or a material layer with a sufficient thickness for preventing the hyperpolarized gas from sampling the underlying substrate. Also, the surface should have a low relaxivity relative to the hyperpolarized gas. As such, both the material and the thickness are chosen and configured to inhibit the surface induced depolarization of the gas. As regards the thickness, it is preferred that the thickness be greater than the critical decay scale length $L_p$ and more preferably is greater than a plurality of the decay length scale. For example, for $^3$He and HDPE, the critical length scale is about 8 $\mu$m so a preferred material layer depth is >about 16–20$\mu$m.

Further, as regards the "low relaxivity", it is preferred that for $^3$He the material have a relaxivity value less than about 0.0013 cm/min and more preferable less than 0.0008 cm/min. For $^{129}$Xe, it is preferred that the material have a relaxivity value less than about 0.012 cm/min and more preferably less than about 0.0023 cm/min. Similarly "reduced solubility" is meant to describe materials for which the hyperpolarized gas has a reduced solubility. Preferably, as regards $^{129}$Xe the solubility is less than about 0.75, and more preferably less than about 0.4. For $^3$He the solubility is preferably less than about 0.03, and more preferably less than about 0.01.

The second layer 44 includes the external surface 12b that is exposed to air which includes components which can be potentially degrading to the hyperpolarized gas in the chamber. For example, as discussed above, paramagnetic oxygen can cause depolarization of the gas if it migrates into the contact surface 12a or the chamber 30. As such, it is preferred that the second layer 44 be configured to suppress oxygen migration. For example, the second layer 44 can be formed as an oxygen resistant substrate, a metal layer, or metallized deposit or coating formed over another layer. Preferably, the second layer prevents de-magnetizing amounts of $O_2$ from entering into the chamber after 24 hours at 1 atm. More preferably, for a desired $T_1$ of about 24 hours and after 24 hours of permeation, it is preferred that the $O_2$ concentration be less than about $2.6 \times 10^{-5}$ amgt. Thus, at 1 atm, for a 1 liter bag, it is preferred that the container be configured to keep the $O_2$ concentration in the chamber below 0.003% of the total gas concentration. Of course, the second layer can be alternatively chosen or configured to shield other environmental contaminants such as moisture. For example, in this embodiment, a first layer may have a very low permeability for $O_2$ but may be sensitive to moisture. The second layer can be configured with a protective polyethylene coating to compensate for this property and provide an improved $T_1$ like container.

In yet another alternative embodiment, the inner surface 12a can be configured as a high purity (non-magnetic) metal film applied to an underlying substrate, polymer, or other container material. High purity metal surfaces can provide even better protection against depolarization relative to other surfaces. Because the hyperpolarized gas contacts the metal, the underlying material does not have to have a low solubility for the hyperpolarized gas. In a preferred embodiment, the container is resiliently configured as a collapsible bag with the inner surface 12a formed from a high purity metal film (preferably a thickness within the range of about 10 nm–10 microns). As such, in this embodiment, the first layer 41 is the metallized layer and can provide the oxygen resistance/shield as well as protection against contact depolarization. Preferred metals include those that are substantially paramagnetically pure (i.e., they do not introduce magnetic moments) and resistant to contact depolarization of the hyperpolarized gases. Stated differently, the metal used should be chosen to minimize the adsorption time of the gas on the metal surface, i.e., such that the noble gas has a low adsorption energy on the metal surface. Examples of suitable materials include, but are not limited to, aluminum, gold, silver, indium, beryllium copper, copper, and mixtures and blends thereof. As used herein, "high purity" includes materials which have less than 1 ppm ferrous or paramagnetic impurities and more preferably less than 1 ppb ferrous or paramagnetic impurities.

In an additional embodiment, the inner surface 12a can be formed as a hybrid surface (a blend or side by side disposition of high purity metal film and polymer) or as a high purity metal formed over a polymer substrate. As such, a metal film can be layered over a polymer with good relaxivity properties to compensate for cracks or gaps which may develop in the metal film layer.

In another preferred embodiment, as shown in FIG. 9, the inner surface 12a is formed directly by the inner wall of a polymer bag and the outer surface is formed by a metallized coating positioned over and directly contacting the polymer bag. However, as illustrated in FIGS. 10 and 11, intermediate layers 42, 43 positioned between the inner layer 41 and outer layer 44 can also be used.

In FIG. 10, the container 10 has four layers 41, 42, 43, 44. As shown, the inner layer 41 is not a coating but is defined by the expandable polymer (or modified polymer) bag having a thickness sufficient to inhibit contact depolarization. In this embodiment the intermediate layers can be formed from any number of alternative materials, preferably resilient materials so as to contract and expand with the inner layer 41. In one embodiment (not shown) a bag with five layers is used: the first layer is 35 $\mu$m of HDPE; the second layer 42 is 35 $\mu$m of polyamide; the third layer 43 is 1 $\mu$m of aluminum; the fourth layer 44 is 35 $\mu$m of polyvinylidene chloride; and the fifth layer (not shown) is 35 $\mu$m of polyester. Advantageously, the multiple layers can provide additional strength and/or puncture and pressure resistance. Of course, alternative materials and numbers of layers can also be employed according to the present invention. In one embodiment (not shown), a coating can be placed on the inner surface 12a of the polymer bag to define the proper depth of the contact layer either alone or in combination with the thickness of the polymer bag. Of course, the two layers can be formed as one layer if the container material employed has a low-relaxivity for the hyperpolarized gas and if the material is sufficiently impermeable to environmental contaminants such as $O_2$. Examples of such materials include but are not limited to PET (polyethylene terphthalate), PVDC (polyvinylidene dichloride), cellophane and polyacrylonitrile.

As shown in FIGS. 13–15, the container 10 also includes a sealing means operably associated with the entry port 22 and used to capture the hyperpolarized gas within the chamber 30. In the configuration shown in FIG. 13, the coupling member 20 includes a conduit 70 extending outwardly therefrom. Generally described, the sealing means closes off the passage 22a (FIG. 3) in communication with the entry port 22, thereby retaining the hyperpolarized gas in the container. Examples of suitable sealing means include, but are not limited to, a clamp 72 (FIG. 13) a heat seal 74 (FIG. 14) and a membrane seal 76 (FIG. 15). Alternatively, a valve, a stop cock, and other fittings and/or seals (gaskets, hydrocarbon grease, O-rings) (not shown) can be used to control the release of the hyperpolarized gas. Preferably, care is taken to insure all fittings, seals, and the like which contact the hyperpolarized gas or which are located relatively near thereto are manufactured from materials which are friendly to polarization or which do not substantially degrade the polarized state of the hyperpolarized gas. For example, as noted above, except for Tedlar™ (polyvinylfluoride), most commercially available seals include fluoropolymers which are not particularly good for the preservation of either $^{129}$Xe or $^3$He hyperpolarized gases because of the solubility of the material with the hyperpolarized gas.

Inasmuch as most common gasket materials are fluoropolymers, they can potentially have a substantially depolarizing effect on the gas. This can be especially acute with respect to $^3$He. This can be attributed to a relatively high solubility of helium in most fluoropolymers due to the larger void space in the polymer attributable to the large fluorine atoms. Indeed, preliminary tests indicate that materials of common O-rings (such as Viton™, Kel-F™, ethylene-propylene, Buna-N™, and silicone) exhibit far worse relaxation properties than pure polymers. Most conventional O-rings are so depolarizing that they can dominate the relaxation of an entire hyperpolarized gas chamber. Indeed, commercial ethylene propylene- O-rings exhibit $\frac{1}{3}$–$\frac{1}{2}$ the relaxation time compared to pure LDPE with $^{129}$Xe. O-ring magnetic impurities can be introduced by such things as colorants and fillers and the like. Therefore, it is preferred that the containers of the present invention employ seals, O-rings, gaskets and the like with substantially pure (substantially without magnetic impurities) hydrocarbon materials such as those containing polyolefins. Examples of polyolefins include polyethylene, polypropylene, copolymers and blends thereof. Additional suitable seals include hydrocarbon grease and hydrocarbon gaskets and O-rings made from polyethylene and the like. Thus, if a valve is used to contain the gas in the chamber 30, it is preferably configured with a magnetically pure (at least the surface) O-ring and/or with hydrocarbon grease. Of course, if fillers and plasticizers are employed, then it is preferred that they be selected to minimize the magnetic impurities such as substantially pure carbon black.

In an alternative embodiment, the O-ring seal can be configured with the exposed surface coated with a high purity metal as discussed for the container surface. Similarly, the O-ring or seal can be coated or formed with an outer exposed layer of a polymer at least "$L_p$" thick. For example, a layer of pure polyethylene can be positioned over a commercial available O-ring. One preferred O-ring material for $^{129}$Xe is a Teflon™ coated rubber O-ring above or a low-relaxivity polymer as discussed above.

FIGS. 13 and 14 illustrate preferred embodiments of a seal arrangement.

Figure 17:
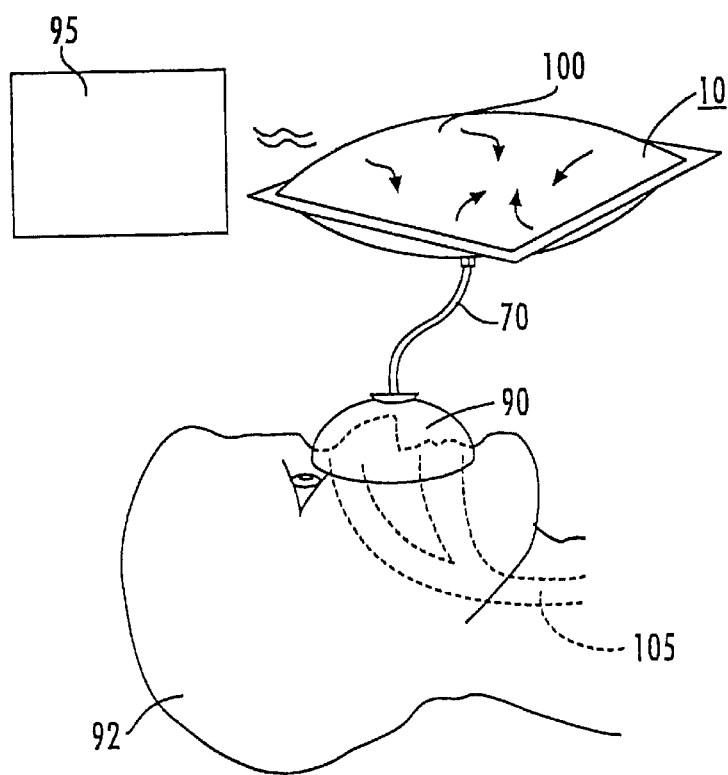
FIG. 17 is a schematic illustration of the resilient container of FIG. 13 shown attached to a user interface adapted to receive the container for delivering the hyperpolarized gas therein to the user according to one embodiment of the present invention.
Figure 18:
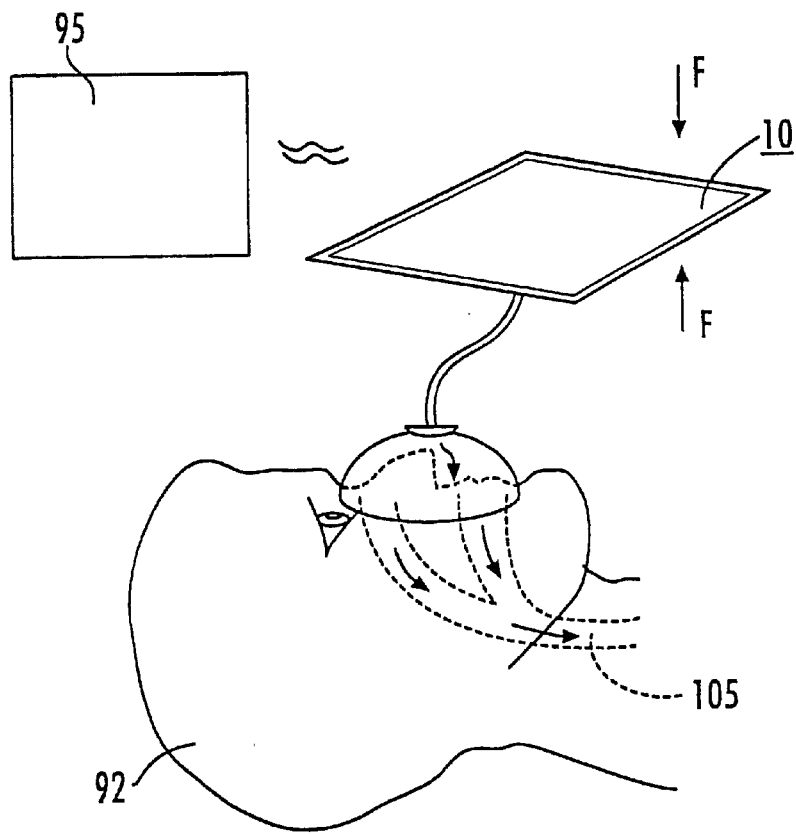
FIG. 18 shows the container of FIG. 17 in a deflated condition after forces on the container cause the hyperpolarized gas to exit the container and enter the target.

Each seals the fluid passage 22a by pinching the conduit 70 shut in at least one position therealong. FIG. 13 shows the use of an external clamp 72 and FIG. 14 shows the use of a redundant heat seal 74. In operation, each is easily employed with little impact on the polarization of the gas in the container 10. For example, for the embodiment shown in FIG. 14, after the container 10 is filled with hyperpolarized gas, an in-process clamp (not shown) is inserted over the conduit 70 such that it closes off the passage 22a. Heat is applied to the conduit 70 as the conduit wall is collapsed to provide a heat seal 74 to at least one side of the in-process clamp. The bag is then ready to transport. Once at the desired delivery location site, the heat seal 74 can be cut away and a temporary clamp can be placed on the conduit 70. As shown in FIG. 17, the conduit 70 can be directly engaged with a breathing apparatus or patient interface 90. As illustrated in FIG. 18, the hyperpolarized gas 100 can be forced out of the bag and into the interface 90 such as by externally depressing/compressing the walls of the container 10. Alternatively, the patient 92 can simply inhale thereby directing the gas 100 into the inhalation pathway 105.

Figure 19:
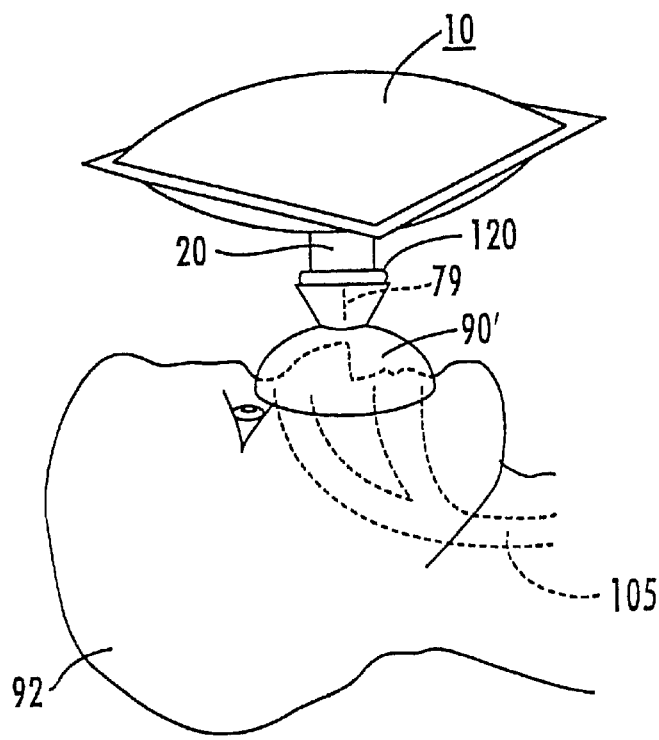
FIG. 19 is a schematic illustration of the container of FIG. 15 shown attached to a user interface according to one embodiment of the present invention.

Turning now to FIG. 15, in another embodiment, a membrane seal 76 is positioned directly over the external portion of the entry port 22. The membrane seal 76 can be attached by heat, or an anchoring member such as a polymer washer threadably attached over the peripheral portion of the coupling member 22, preferably leaving the central portion 76a externally accessible. In this embodiment, as shown in FIG. 19, the container 10 can be transported to the use site and inserted directly into a patient interface 90'. Preferably, the membrane seal 76 is inserted into the interface 90' such that it is positioned internal to the air tight coupling provided by the joint 130 between the coupling member 20 and the interface 90'. Advantageously, the interface 90' can include a puncture 79 recessed within the receiving area to open the central portion of the membrane seal 76 after the coupling member 20 forms the external joint 130 such that the container is sealed to the interface 90'. This allows the gas in the container to be easily released and directed to the patient. The gas can be easily extracted or forced out of the container 10 by depressing the walls 12, 13 of the container 10 or via inhalation. Advantageously, such a configuration removes the requirement for relatively complex or sophisticated gas extraction mechanisms and also reduces the amount of physical manipulation and/or interfaces required to deliver the gas to the subject.

Figure 16:
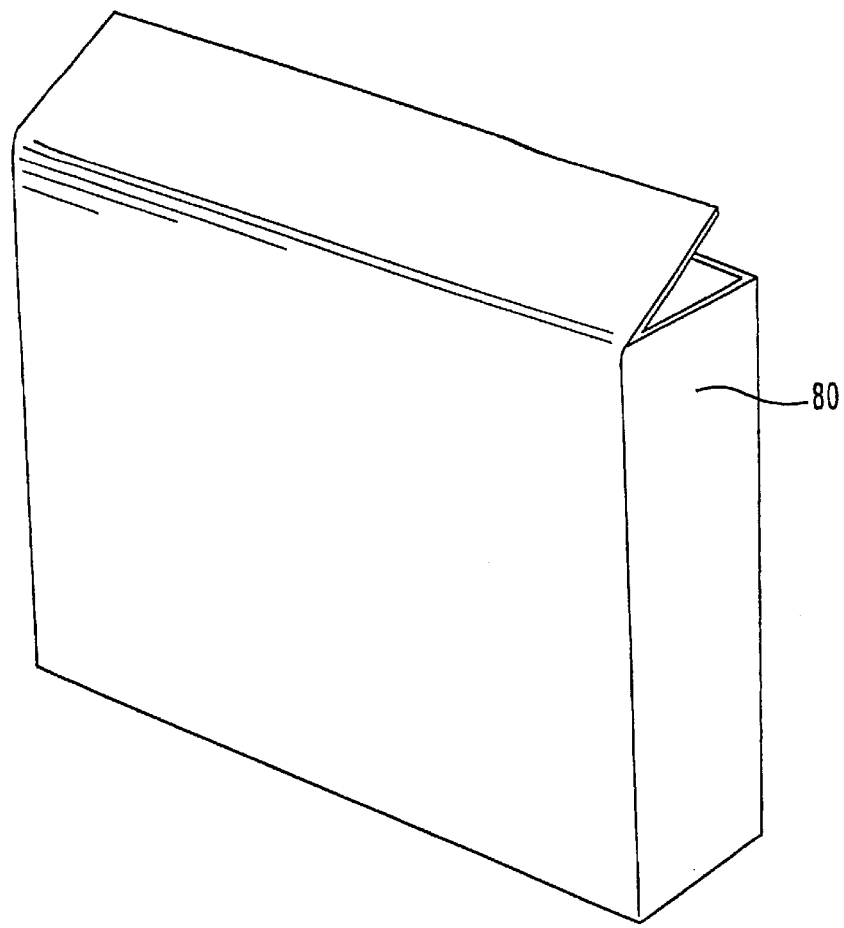
FIG. 16 is a side perspective view of a shielded shipping receptacle configured to receive the container according to one embodiment of the present invention.

As shown in FIG. 16, a shipping box 80 is preferably used to hold the bag 10 during transport. This can help protect the bag from physical hazards. In addition, it is preferred that the box 80 include magnet means to provide a desired static magnetic (substantially homogeneous) field around the hyperpolarized gas. In addition, or alternatively, the box 80 can be configured to form a shield from undesirable stray magnetic fields as will be discussed further below.

In summary, the present invention provides containers which improve on the relaxation time of the hyperpolarized gas. Preferably, the container is sized and configured and the contact surface formed from a suitable material such that the hyperpolarized gas in the container has a relaxation time greater than about 6 hours and more preferable greater than about 20 hours for $^3$He. Similarly, the container is preferably sized and configured such and the contact surfaces formed from a suitable material that the $^{129}$Xe hyperpolarized gas in the container has a relaxation time greater than about 4 hours and more preferably greater than about 8 hours.

Shielding

Unless special precautions are taken, relaxation due to stray magnetic fields can dominate all other relaxation mechanisms. Both gradients in the static field experienced by the gas and low-frequency oscillating magnetic fields can cause significant relaxation. Based on recent experience, oscillating fields are the biggest potential concern.

At all relevant pressures and field strengths, the relaxation rate due to static field inhomogeneities is given by (2.40).

$$\Gamma_{\nabla B} = \frac{Do}{P}\left|\frac{\nabla_T B_O}{B_O}\right|^2 \quad (2.40)$$

where "$B_0$" is the static applied field, "$\nabla_T$" is the transverse gradient of that field, "$D_0$" is the diffusion constant of the hyperpolarized gas at one atmosphere, and "P" is the gas pressure. For 1 atmosphere of He ($D_0$ is≈2 cm$^2$/s) in the earth's field (0.5 Gauss), a transverse gradient of 5 mG per cm leads to $\Gamma \nabla_B \approx 10^{-4} S^{-1}$ and a gradient induced relaxation time "$T_1$" of approximately 1.5 hours. During transport, it is desirable to avoid inhomogeneous fields due to nearby objects. Calculations can estimate the types of gradient strengths that can be expected from objects like car frames and axles. Another way to be less sensitive to such unpredictable gradient relaxation is to apply an external field "B" which is sufficiently homogeneous (thus, not raising $\nabla_T B$). In the previous example, if a homogeneous field of even 10 G were applied, the same 5 mG gradient would instead result in $T_1 \approx 600$ hr. Preferably, the homogenity is about $5 \times 10^{-4}$ over a 1×1×1 cm cube.

In addition to static field gradients, oscillating magnetic fields can cause significant depolarization. Such oscillating fields can be generated by car engines, power substations, and other large, current carrying entities. Incoherent fields with a correlation time ($t_c << 1/\gamma B_{noise}$) can be shown to lead to negligible relaxation, though they will likely contain spectral components which are resonant with the polarized gas. However, there is evidence that automobile engines can generate coherent fields of up to about a milliGauss in the 500 Hz range (the resonant frequency of $^{129}$Xe in the earth's field). The resonant frequency of $^3$He in the earth's field is 1.6 Khz.

The relaxation rate due to coherent alternating current fields is given by $$\Gamma_{AC} = 2\gamma B_{AC} \quad (2.41)$$

For example, a 5 microGauss resonant field ($B_{AC}$) leads to a $^{129}$Xe relaxation time of about 100 seconds. In order to minimize this rate, the AC field is preferably blocked, the static magnetic field ($B_0$) is increased (to increase the resonant frequency of gas), or both. Preferably, AC fields are shielded by positioning a shield or shipping container formed of ordinary metals proximate to (around) the hyperpolarized gas in the container. The skin depth or spatial decay constant of an electromagnetic wave in a metal is given by $$\delta = (\rho/\pi f \mu)^{1/2} \quad (2.42)$$

where "$\rho$" is the resistivity of the shielding metal, "f" is the frequency (in Hz) of the field, and "$\mu$" is the permeability of the metal. Each skin depth "$\delta$" reduces the external magnetic field associated with the AC source $B_{AC}$ by a factor of 1/e. To reduce "$B_{AC}$" by a factor of 100, preferably about five skin depths are used. At room temperature, the skin depth of aluminum is $\delta_{Al}$ (500 Hz)=4 mm. Thus, for a factor of 100 reduction in AC field strength "$B_{AC}$" one can use approximately ¾ inch of aluminum. Alternatively, the shield can use about 0.1 mm of ultra low carbon steel (by virtue of its greater permeability). However, use of high permeability materials may also shield a large portion of the earth's magnetic field from the hyperpolarized sample, lowering its resonant frequency and increasing the likelihood of depolarization. Again, application of a homogeneous static field proximate to the hyperpolarized gas can help by pushing the resonant frequency of the gas outside the bandwidth of common AC fields. For $^{129}$Xe, the static field is preferably at least about 20 gauss; and for $^3$He, the static field is preferably at least about 8 gauss. This will shift the $^{129}$Xe resonant frequency to 23.6 Khz and the $^3$He resonant frequency to 25.6 Khz. Preferably the frequency will be above 10 Khz.

When the hyperpolarized gas is $^3$He, it is preferred that the sealed container have a pressure in the range of about 1–10 atm (10 atm, 75 hours). Higher pressures allow more product to be shipped in the container and reduces the sensitivity of the hyperpolarized gas to gradient relaxation, but the gas-gas collision relaxation can become substantial. In contrast, for $^{129}$Xe, it is preferred that the gas pressure be about 1 atm or less, because higher pressures can dramatically reduce the expected relaxation time of the hyperpolarized $^{129}$Xe (10 atm, 5.6 hours). It is also preferred that the container be configured as a single dose unit, such as with 1 liter of a hyperpolarized gas product.

Preconditioning the Container

Preferably, due to susceptibility of the hyperpolarized to paramagnetic oxygen as noted above, the storage container 10 is preconditioned to remove contaminants. That is, it is processed to reduce or remove the paramagnetic gases such as oxygen from within the chamber and container walls. For containers made with rigid substrates, such as Pyrex™ UHV vacuum pumps can be connected to the container to extract the oxygen. However, for resilient containers such as polymer bag containers, a roughing pump can be used which is typically cheaper and easier than the UHV vacuum pump based process. Preferably, the bag is processed with several purge/pump cycles, eg., pumping at or below 40 mtorr for one minute, and then directing clean buffer gas (such as nitrogen) into the container at a pressure of about one atm or until the bag is substantially inflated. The oxygen partial pressure is then reduced in the container. This can be done with a vacuum but it is preferred that it be done with nitrogen. Once the oxygen realizes the partial pressure imbalance across the container walls it will outgas to re-establish equilibrium. Typical oxygen solubilities are on the order of 0.01–0.05; thus, 95–99% of the oxygen trapped in the walls will transition to a gas phase. Prior to use, or filling, the container is evacuated, thus harmlessly removing the gaseous oxygen. Unlike conventional rigid containers, polymer bag containers can continue to outgas (trapped gases can migrate to the chamber because of pressure differentials between the outer surface and the inner surface) even after the initial purge pump cycles. Thus, care should be taken to minimize this behavior especially when the final filling is not temporally performed with the preconditioning of the container. Preferably, a quantity of clean filler gas is directed into the bag (to substantially equalize the pressure between the chamber and ambient conditions) and sealed for storage in order to minimize the amount of further outgassing that may occur when the bag is stored and exposed to ambient conditions. This should substantially stabilize or minimize any further outgassing of the polymer or container wall materials. In any event, the filler gas is preferably removed (vacuumed) prior to final filling with the hyperpolarized gas. Advantageously, the container of the instant invention can be economically reprocessed (purged, cleaned, etc.) and reused to ship additional quantities of hyperpolarized gases.

It is also preferred that the container or bag be sterilized prior to introducing the hyperpolarized product therein. As used herein the term "sterilized" includes cleaning containers and contact surfaces such that the container is sufficiently clean to inhibit contamination of the product such that it is suitable for medical and medicinal purposes. In this way, the sterilized container allows for a substantially sterile and non-toxic hyperpolarized product to be delivered for in vivo introduction into the patient. Suitable sterilization and cleaning methods are well known to those of skill in the art.

Measuring Gas Solubility in a Polymer or Liquid

In the past, measuring gas solubilities of most polymers has been time consuming and difficult, and in the case of helium, usually inaccurate. However, as discussed above, the hyperpolarized gas relaxation time, $T_1$, is now determined to be proportional to gas solubility. Advantageously, due to the recognition and determination of the relationships discussed above, hyperpolarized noble gases such as $^3$He and $^{129}$Xe can be used to determine or measure the gas solubility in a polymer or liquid. This information can be valuable for quickly assessing the structures of the polymer. In addition, a given polymer sample can be evaluated using both $^{129}$Xe and $^3$He gases, as each can give complimentary information. For example, $^3$He will sample a greater depth of the polymer based on its greater diffusion coefficients.

Figure 20:
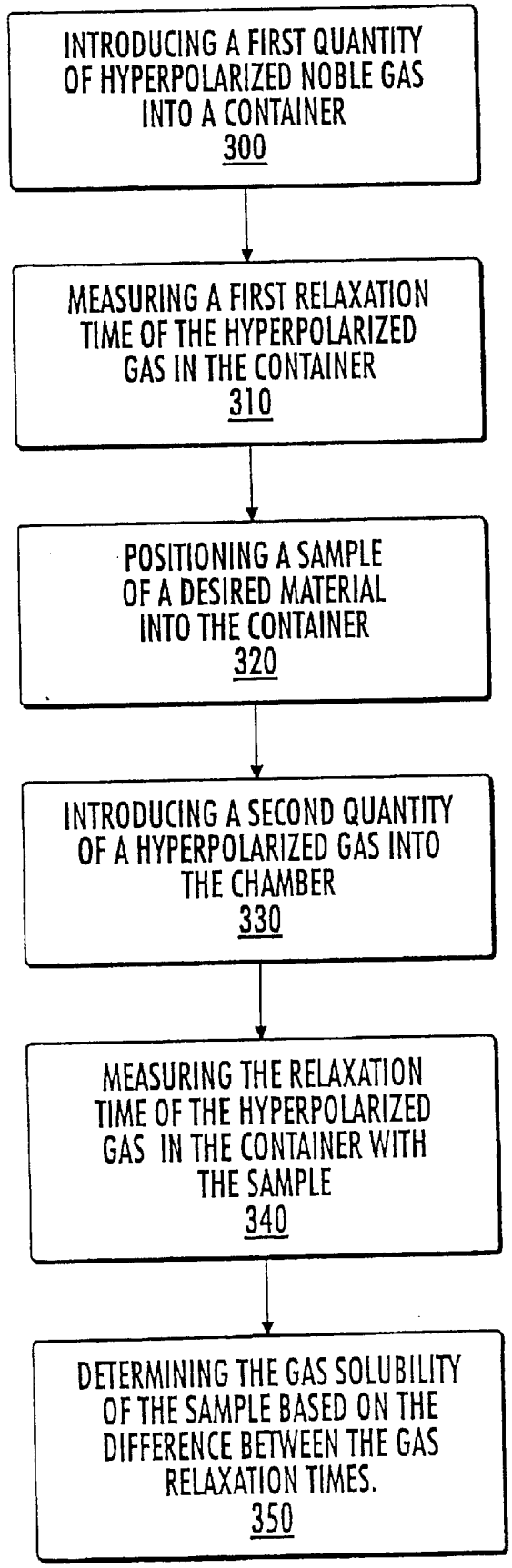
FIG. 20 is a block diagram of a method for determining gas solubility in a polymer according to one embodiment of the present invention.

Preferably, as shown in FIG. 20, a first quantity of a hyperpolarized gas is introduced into a container (Block 300). A first relaxation time is measured of the 25 hyperpolarized gas in the container (Block 310). A selected material sample is positioned in the container (Block 320). A second quantity of a hyperpolarized noble gas is introduced into the container (Block 330). A second relaxation time is measured associated with the sample and the gas in the container (Block 340). The gas solubility is determined based on the difference between the two relaxation times (Block 350). Preferably this is determined according to equation (2.23c). The material sample can be a physical or solid sample or a liquid as described above.

Although the sample used above was a geometrically fixed polymer sample, the method can also be used to determine gas solubilities in liquids or fluids. For example, instead of placing a polymer sample into the chamber, a liquid can be introduced. The liquid will preferably be introduced in a quantity which is less than the free volume of the chamber as it will conform to the shape of the chamber to define an associated volume and surface area. The polarized gas can then be directed into the chamber with the liquid and the relaxation rate determined due to the specific liquid. This can be especially helpful in formulating carrier substances for injection formulations of hyperpolarized $^{129}$Xe and $^3$He.

EXAMPLES

In the examples provided below, the polymer contact surface is assumed to be present at a depth corresponding to a plurality of critical length scales as discussed above.

Example 1

$^3$He LDPE/HDPE Bag

An exemplary one liter patient delivery bag, such as is shown in FIG. 7, is a 7 inch×7 inch square. The expected $T_1$ for $^3$He can be determined using (Equation 2.4) and the theoretical relaxivity of LDPE for $^3$He quoted in Table 4.3. The associated area (A=2*18 cm*18 cm) is 648 cm$^2$, the volume is 1000 cubic centimeters, and the relaxivity is 0.0012 cm/min. Equation 2.4 leads to a $T_1$ of about 1286 min or 21.4 hours for an LDPE bag configured and sized as noted above (absent other relaxation mechanisms). For a bag made of HDPE, which has a lower relaxivity value of about 0.0008 cm/min (attributed to the lower $^3$He solubility), the $T_1$ is estimated at 32 hours. In deuterated HDPE the $T_1$ is expected to be about 132 hours.

Example 2

$^{129}$Xe LDPE/Nylon Bag

The same 1 liter LDPE patient delivery bag as described in Example 1 contains hyperpolarized $^{129}$Xe. Volume and surface area are the same but the theoretical relaxivity is 0.0419 cm/min (Table 4.2) for $^{129}$Xe on LDPE. The relaxivity is much higher because of the higher solubility of $^{129}$Xe in LDPE compared to He ($S_{Xe}$=0.68 vs $S_{He}$=0.006). For this configuration, $T_1$ is estimated at 36.8 minutes. Similarly, for the measured relaxivity for Nylon-6 of 0.0104 cm/min, predict $T_1$ is predicted to be about 148 min or about 2.4 hours. This value is close to what has been measured for the presently used Tedlar™ bags.

Example 3

Metal Film Surface

In this example, metal film coatings are used as the contact surface. The 7"×7" square bag described in Example 1 is employed but coated or formed with high purity aluminum on its internal contact surface (the surface in contact with the hyperpolarized gas). The relaxivity of high purity aluminum for $^{129}$Xe has been recently measured to be about 0.00225 cm/min. (One readily available material suitable for use is Reynold's™ heavy duty freezer foil). Doing the calculation, one can obtain a container with an extended $T_1$ for xenon of about 11.43 hours. This is a great improvement in $T_1$ for Xe. Similarly, the use of such metal film surfaces for 3He can generate $T_1$'s in the range of 1000's of hours (the container no longer being a limiting factor as these $T_1$'s are above the theoretical collisional relaxation time described above). Metals other than aluminum which can be used include indium, gold, zinc, tin, copper, bismuth, silver, niobium, and oxides thereof. Preferably, "high purity" metals are employed (i.e., metals which are substantially free of paramagnetic or ferrous impurities) because even minute amounts of undesirable materials or contaminants can degrade the surface. For example, another high purity aluminum sample tested had a relaxivity of about 0.049 cm/min, a full 22 times worse than the sample quoted above. This is most likely due to the presence of ferrous or paramagnetic impurities such as iron, nickel, cobalt, chromium and the like. Preferably, the metal is chosen such that it is well below 1 ppm in ferrous or paramagnetic impurity content.

Example 4

Multiple Materials

Using the bag configured as noted in Example 1, one can determine the effects of the addition of multiple materials. For example, a 5 cm$^2$ silicone gasket positioned on the 1 liter deuterated HDPE bag (described in Example 1 (for $^3$He)) with a starting $T_1$ of 132 hours will reduce the container's associated relaxation time. As pointed out in Equations 2.5, 2.6, relaxation rates are additive. Thus, to properly determine the container or equipment relaxation time, the relaxivities and corresponding surface areas of all the materials adjacent the free volume should be evaluated. The hypothetical silicone gasket, with an exemplary area "A" of 5 cm$^2$, the measured relaxivity of 0.0386 cm/min (p. 47, table 4.3), and free volume still at 1000 cc, gives a relaxation rate of about 1.9×10$^{-4}$/min. Adding the rate due to the bag itself (1.3×10$^{-4}$/min) yields a total rate of about 3.2×10$^{-4}$/min which is inverted to get a $T_1$ of about 52 hours. Therefore, it is apparent that adding a very small surface area of a poor material can drastically shorten the $T_1$ despite the fact that most of the container material is good. Of course, real life O-ring materials can have relaxivities an order of magnitude higher than the one described, making the situation even worse. Thus, it is important to use substantially pure (impurity free) materials. The relaxivity for an available "off the shelf" silicone O-ring for $^{129}Xe$ was measured at about 0.2–0.3 cm/min. For example, using the measured $^{129}Xe$ relaxivity numbers for the $^3He$ deuterated HDPE container will reduce the 132 hour bag down to just 15 hours (a full order of magnitude deterioration). The key is that every gasket, coupling, valve, tubing or other component that is added to the bag or container (especially those that are in fluid communication with the hyperpolarized gas) is preferably made of the friendliest possible material relative to the hyperpolarized state.

Example 5

Measurement of Specific Material Properties

Measurement of specific material properties such as the relaxivities of materials is described above. For example, as noted in equation 2.5, relaxation rates attributed to various relaxation mechanisms are additive. Therefore, in order to measure the specific material property, a spin-down chamber such as that described herein can be used to determine two relaxation times for a hyperpolarized gas. Using the chamber consisting of two hemispheres sealed with an O-ring, the chamber is closed, HP ("hyperpolarized gas") is introduced therein, and the relaxation time $T_1$ is measured. Then the chamber is opened, a sample of known surface area is inserted, and the process is repeated to measure a new $T_1$. The new $T_1$ will be less than the old because a new relaxing surface has been added while keeping the free volume roughly the same. The difference between the two relaxation times is attributed to the relaxivity of the added material specimen. Thus, the difference can be used to calculate the material relaxivity using equation (2.10).

Example 6

Validation of the Sorption Model

FIGS. 4.1 and 4.2 show the calculated and experimental $T_1$ values for $^{129}Xe$ and $^3He$, respectively, in a 1 cc sphere for different surface materials as plotted against the product of solubility (S) and the square root of the molar density of protons in the material matrix $[1H]^{.5}$. The 1 cc sphere value incorporates both volume and surface area and is a useful $T_1$ metric corresponding to conventional evaluations, and as such is typically more readily descriptive than the relaxivity parameters described herein. The $T_1$ value according to equation (2.23c) depends on a number of fixed constants and then depends inversely on gas solubility and the square root of the proton concentration. Experimental values of the measured one cubic centimeter sphere $T_1$ ($T_1^{cc}$) for all the polymers are plotted as well and show substantial agreement between theory and experiment, thus validating the sorption model described herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A resilient container for holding hyperpolarized gas, comprising:
  a compressible body comprising at least one collapsible wall and an internal gas holding chamber, wherein said wall changes its shape responsive to the introduction of gas into and out of said internal chamber such that said wall has a collapsed configuration associated with the absence of a gas held in said internal chamber and an expanded configuration associated with the presence of a sufficient quantity of gas held in said internal chamber, wherein said at least one wall comprises:
  a first layer of a first material configured to define the inner surface of said internal chamber;
  a second layer of a second material attached to and positioned to overlie said first layer such that said first layer is between said second layer and said internal chamber;
  a sealable port positioned in said wall in fluid communication with said internal chamber for directing gas in and out of said internal gas holding chamber; and
  a quantity of hyperpolarized gas positioned in said internal gas holding chamber.

2. A resilient container according to claim 1, wherein at least one of said first and second layer materials is an oxygen shielding material, and wherein said first and second layers are concurrently responsive to the application of pressure.

3. A resilient container according to claim 2, wherein said first layer has a thickness sufficient to inhibit the hyperpolarized gas from exiting said first layer into said second layer, and wherein said first layer material has a low relaxivity for said hyperpolarized gas.

4. A resilient container according to claim 3, wherein said first layer comprises a polymer gas-contacting surface.

5. A resilient container according to claim 2, wherein said hyperpolarized gas is $^3He$, and wherein said first layer material is chosen from the group consisting of polyolefin, polystyrene, polymethacrylate, polyvinyl, polydiene, polyester, polycarbonate, polyamide, polyimide, polynitriles, cellulose and cellulose derivatives, and blends and mixtures thereof.

6. A resilient container according to claim 5, wherein said first material is perdeuterated or partially perdeuterated.

7. A resilient container according to claim 6, wherein said first layer material is substantially free of paramagnetic contaminants.

8. A resilient container according to claim 2, wherein said first layer material comprises a copolymer.

9. A resilient container according to claim 1, wherein said first layer material is chosen from the group consisting of high-density polyethylene, polypropylene having about 50% crystallinity, polyvinylfluoride, polyamide, polyimide, polynitriles, and cellulose, and blends and mixtures thereof.

10. A resilient container according to claim 9, wherein said first layer material is at least partially perdeuterated.

11. A resilient container according to claim 1, wherein said first layer material comprises a high purity metal.

12. A resilient container according to claim 1, wherein said first layer material comprises a material chosen from the group consisting of: aluminum, indium, gold, zinc, tin, copper, bismuth, silver, niobium, and oxides thereof.

13. A resilient container according to claim 1, wherein said hyperpolarized gas is $^3$Helium, and wherein said first material has a relaxivity value of less than about 0.0013 cm/min.

14. A resilient container according to claim 1, wherein said hyperpolarized gas is $^{129}$Xe, and wherein said first material has a relaxivity value of less than about 0.012 cm/min.

15. A resilient container according to claim 1, wherein said hyperpolarized gas is $^3$He, and wherein said gas in said container has a relaxation time longer than about 6 hours.

16. A resilient container according to claim 1, wherein said hyperpolarized gas is $^3$He, and wherein said hyperpolarized gas in said container has a relaxation time longer than about 20 hours.

17. A resilient container according to claim 1, wherein said hyperpolarized gas is $^{129}$Xe, and wherein said hyperpolarized gas in said container has a relaxation time longer than about 4 hours.

18. A method for determining the hyperpolarized gas solubility in a material such as a polymer or fluid, comprising the steps of:
    introducing a first quantity of hyperpolarized gas into a container;
    measuring a first relaxation time of the hyperpolarized gas in the container;
    positioning a sample of a desired material in the container;
    introducing a second quantity of the hyperpolarized noble gas into the container;
    measuring a second relaxation time of the hyperpolarized gas in the container; and
    determining the gas solubility of the sample based on the difference between the first and second relaxation times.

19. A resilient container for holding a quantity of hyperpolarized gas therein, said container comprising:
    a resilient body defined by at least one wall comprising inner and outer surfaces configured to define a gas holding chamber such that said body wall has a first collapsed position and a second inflated position associated with an unfilled and filled chamber, respectively; and
    a quantity of hyperpolarized noble gas held in said chamber;
    wherein said resilient body wall inner surface comprises a metallic material which defines the gas-contacting surface and which inhibits contact-induced polarization loss of said hyperpolarized gas held in said chamber; and
    wherein said resilient body is configured to inhibit the migration of oxygen into said chamber.

20. A resilient container according to claim 19, wherein said wall inner surface is formed of a high purity metal.

21. A resilient container according to claim 19, wherein said wall outer surface is formed of a high purity metal.

22. A resilient container according to claim 19, wherein said wall includes a first layer of a first material and a second layer of a second material, said second material being different from said first material, said second layer positioned on said inflatable body such that said first layer is positioned between said second layer and said chamber, and wherein said first and second layers are concurrently responsive to the application of pressure onto said resilient body.

23. A resilient container according to claim 22, wherein said first layer comprises a material chosen from the group consisting of: polyolefin, polystyrene, polymethacrylate, polyvinyl, polydiene, polyester, polycarbonate, polyamide, polyimide, polynitriles, cellulose and cellulose derivatives, and blends and mixtures thereof, and wherein said metallic inner surface is formed onto said first layer material.

24. A resilient container according to claim 23, wherein said first layer material is at least partially perdeuterated.

25. A resilient container according to claim 23, wherein said first material is substantially free of paramagnetic contaminants.

26. A resilient container according to claim 22, wherein said container chamber has an internal volume (V) and an internal surface area (A), and wherein said container is sized such that the ratio of A to V is less than about 0.75 cm$^{-1}$.

27. A resilient container according to claim 22, wherein said wall includes at least one additional intermediate layer sandwiched between said first and second layers.

28. A resilient container according to claim 22, wherein said first layer is a metal film layer.

29. A resilient container according to claim 22, wherein said first layer material comprises a copolymer, and wherein said metallic inner surface is deposited onto said first layer material.

30. A resilient container according to claim 22, wherein said first layer material is chosen from the group consisting of: high-density polyethylene, polypropylene having about 50% crystallinity, polyvinylfluoride, polyamide, polyimide, polynitriles, and cellulose, and blends and mixtures thereof, and wherein said metallic inner surface is formed onto said first layer material.

31. A resilient container according to claim 30, wherein said first material is perdeuterated or partially perdeuterated.

32. A resilient container according to claim 22, wherein said first layer material is a high purity metal which defines said metallic inner surface.

33. A resilient container according to claim 32, wherein said first layer comprises a material chosen from the group consisting of: aluminum, indium, gold, zinc, tin, copper, bismuth, silver, niobium, and oxides thereof.

34. A resilient container according to claim 19, wherein said hyperpolarized gas is $^3$Helium, and wherein said inner surface material has a relaxivity value of less than about 0.0013 cm/min.

35. A resilient container according to claim 19, wherein said hyperpolarized gas is $^{129}$Xe, and wherein said inner surface material has a relaxivity value of less than about 0.012 cm/min.

36. A method according to claim 18, wherein said sample is a structurally fixed sample having a known geometric shape with a surface formed of the desired material.

37. A method according to claim 18, wherein said sample is a quantity of fluid filling a portion of the free volume in the chamber.

38. A method for filling a container having a collapsible body, comprising the steps of:
    providing a container body with a gas holding chamber such that the container body expands and collapses in response to the filling and purging of gas directed into and out of the chamber, respectively, wherein the internal gas-contacting surface of the container body is formed with a high purity metal to inhibit the contact depolarization attributed thereto;

directing a quantity of hyperpolarized gas into said container body;

expanding the container body by accumulating a quantity of hyperpolarized gas in the gas holding chamber to hold the hyperpolarized gas therein; and sealing the container body to retain the accumulated quantity of gas therein.

39. A method according to claim 38, wherein said forming step comprises positioning a port and a seal for closing said port in said container body such that said gas holding chamber is in fluid communication therewith, said method further comprising the step of configuring the container body such that it inhibits the migration of oxygen into said gas holding chamber when said port is closed.

40. A method according to claim 38, wherein said hyperpolarized gas is $^3$Helium, and wherein said internal gas-contacting surface material has a relaxivity value of less than about 0.0013 cm/min.

41. A method according to claim 38, wherein said hyperpolarized gas is $^{129}$Xe, and wherein said internal gas-contacting surface material has a relaxivity value of less than about 0.012 cm/min.

42. A method according to claim 38, wherein said container body comprises a plurality of overlying material layers attached theretogether so as to be concurrently responsive to the application of pressure thereagainst.

43. A method according to claim 42, wherein each of said plurality of material layers is formed of different materials.

44. A method according to claim 42, wherein said hyperpolarized noble gas held in said container is $^3$He, and wherein said hyperpolarized $^3$He gas in said container has a relaxation time longer than about 6 hours.

45. A method according to claim 42, wherein said hyperpolarized noble gas held in said container is $^3$He, and wherein said hyperpolarized $^3$He gas in said container has a relaxation time longer than about 20 hours.

46. A method according to claim 42, further comprising the step of substantially purging the bag of oxygen before said directing step.

* * * * *